United States Patent
Brown et al.

(10) Patent No.: US 8,696,757 B2
(45) Date of Patent: *Apr. 15, 2014

(54) PROSTHETIC HIP DEVICE AND ASSOCIATED METHOD

(75) Inventors: David R. Brown, Warsaw, IN (US); John R. White, Winona Lake, IN (US); Mark A. Bollinger, Fort Wayne, IN (US); Brian M. May, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 77 days.

This patent is subject to a terminal disclaimer.

(21) Appl. No.: 13/285,426

(22) Filed: Oct. 31, 2011

(65) Prior Publication Data

US 2012/0046755 A1 Feb. 23, 2012

Related U.S. Application Data

(63) Continuation of application No. 11/385,004, filed on Mar. 20, 2006, now Pat. No. 8,048,166, which is a continuation-in-part of application No. 10/838,885, filed on May 4, 2004, now Pat. No. 7,670,383.

(51) Int. Cl.
A61F 2/32 (2006.01)

(52) U.S. Cl.
USPC ....................................................... 623/22.21

(58) Field of Classification Search
USPC .......... 623/16.11, 18.11, 22.11, 22.21, 22.22, 623/22.23
See application file for complete search history.

(56) References Cited

U.S. PATENT DOCUMENTS

| | | | | |
|---|---|---|---|---|
| 4,743,260 A | * | 5/1988 | Burton | 128/898 |
| 4,883,489 A | * | 11/1989 | Grundei et al. | 623/22.36 |

* cited by examiner

*Primary Examiner* — Anu Ramana
(74) *Attorney, Agent, or Firm* — Harness, Dickey

(57) ABSTRACT

A prosthetic device for replacement of a first pelvic portion of a pelvis of a patient opposite to a second pelvic portion relative to a median plane includes an acetabular component a flange component and a pubis component. The acetabular component has a first connecting portion and a second connecting portion at an angle relative to the first connecting portion, the angle selected for a corresponding anatomy of the patient. The flange component is coupled to the first connecting portion and configured to attach to a healthy pelvic portion on a same side of the median plane from the first pelvic portion. The pubis component is connected to the second connecting portion of the acetabular component and having a clamping portion configured to attach to a healthy pubis bone on an opposite side of the median plane from the first pelvic portion.

21 Claims, 22 Drawing Sheets

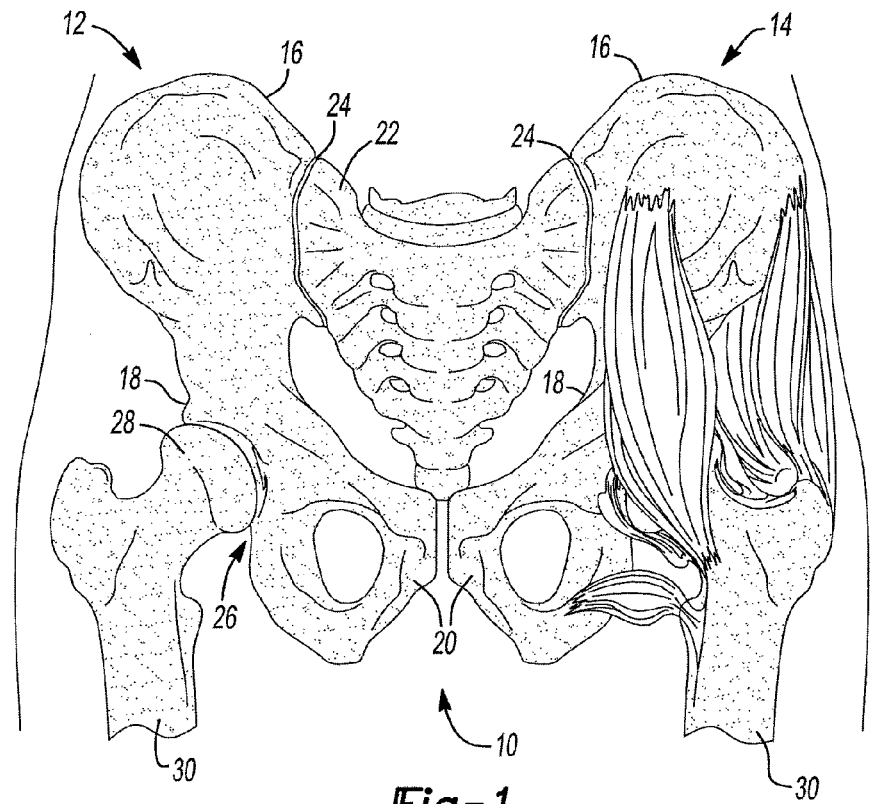
Fig-1
PRIOR ART
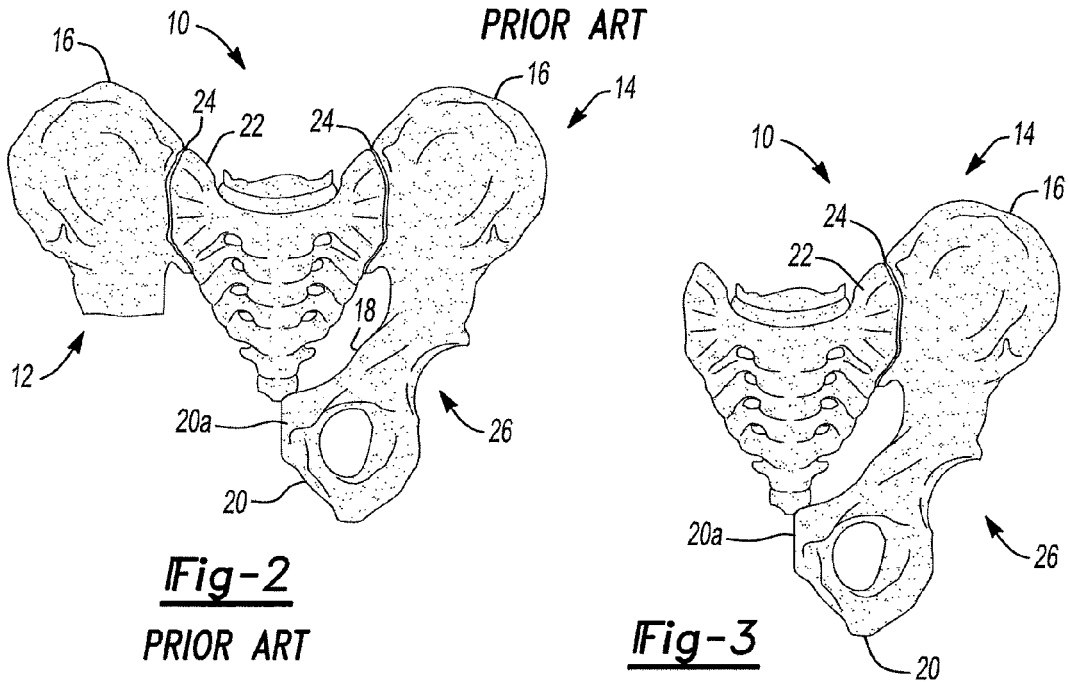
Fig-2
PRIOR ART
Fig-3
PRIOR ART

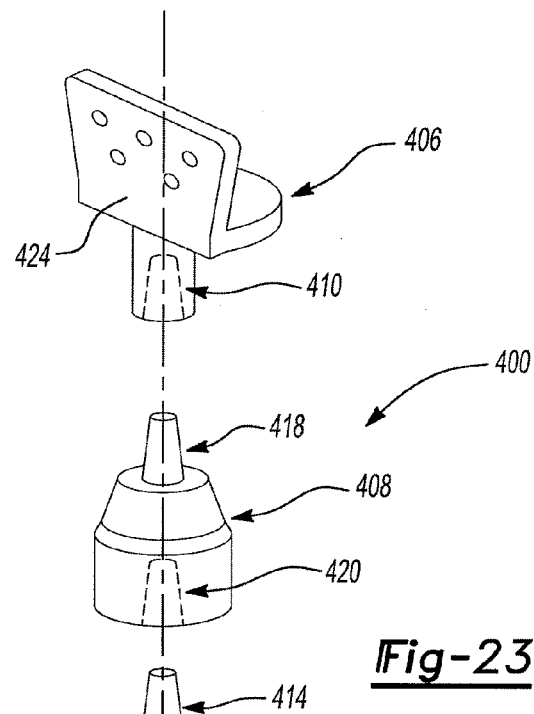
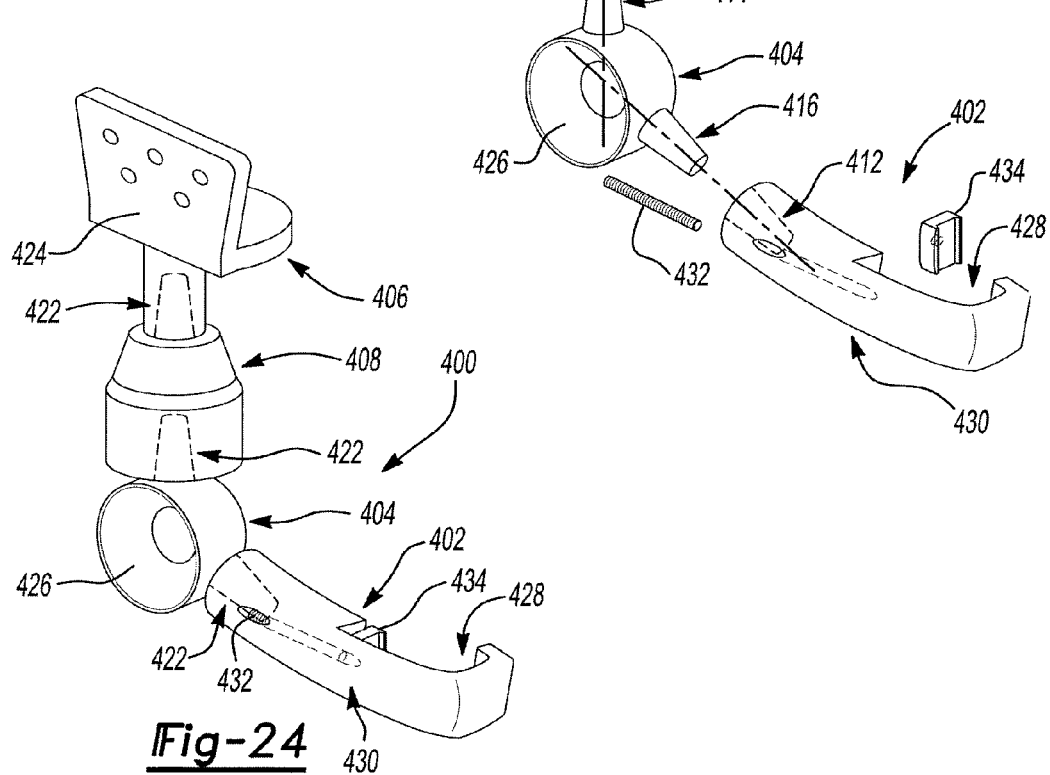

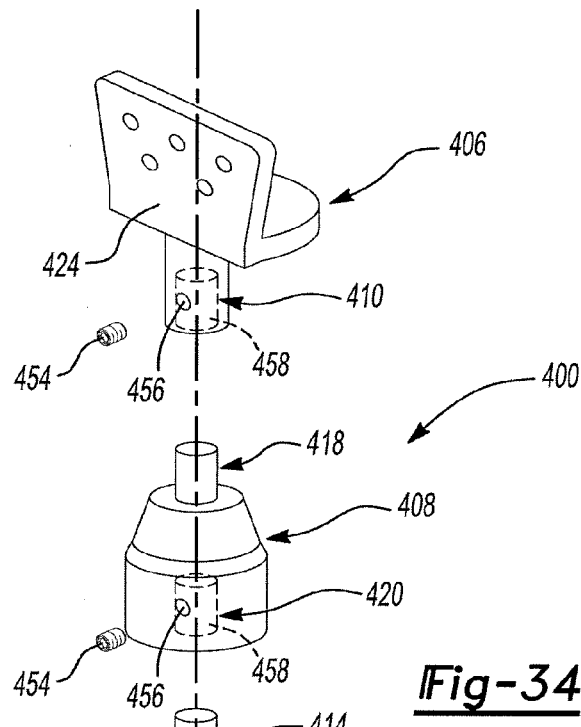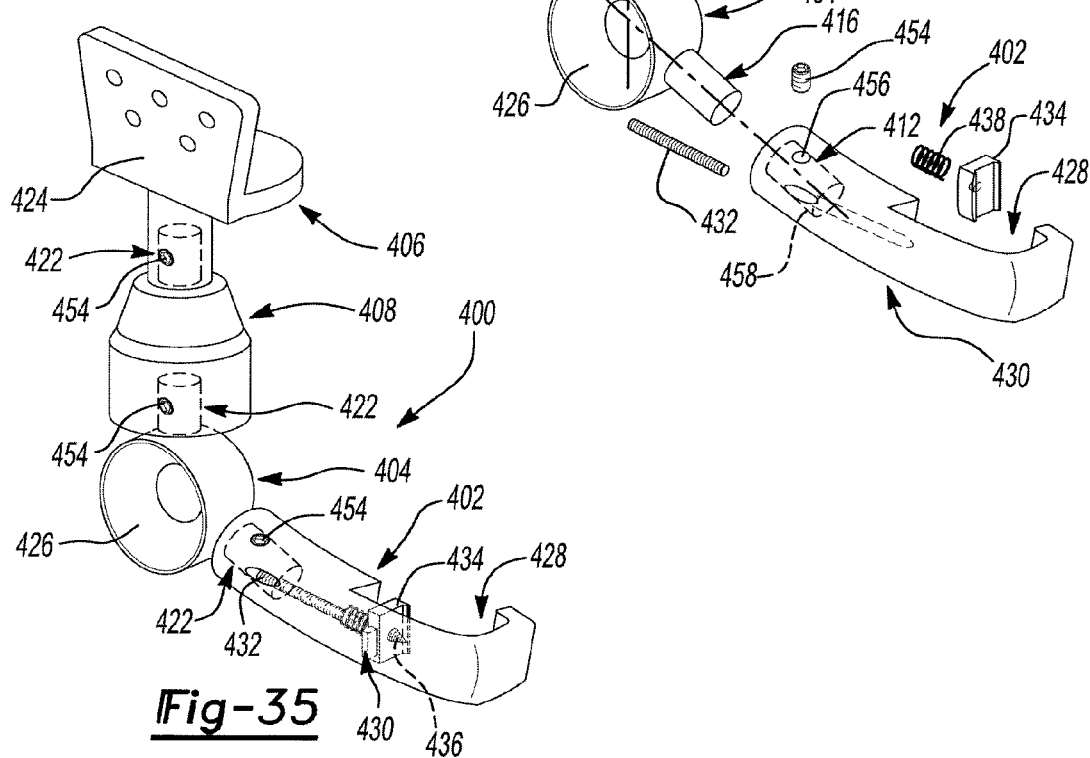

PROSTHETIC HIP DEVICE AND ASSOCIATED METHOD

CROSS-REFERENCE TO RELATED APPLICATIONS

This application is a continuation of U.S. patent application Ser. No. 11/385,004 filed on Mar. 20, 2006, now U.S. Pat. No. 8,048,166 issued on Nov. 1, 2011, which is a continuation-in-part of U.S. patent application Ser. No. 10/838,885, filed on May 4, 2004, now U.S. Pat. No. 7,670,383 issued on Mar. 2, 2010.

This application is related to the following references: U.S. patent application Ser. No. 11/326,561 filed on Jan. 5, 2006, now U.S. Pat. No. 7,476,254 issued on Jan. 13, 2009. U.S. patent application Ser. No. 11/351,227 filed Feb. 9, 2006, now U.S. Pat. No. 7,722,678 issued on May 25, 2010. U.S. patent application Ser. No. 10/797,692 filed Mar. 9, 2004, now U.S. Pat. No. 7,141,073 issued on Nov. 28, 2006. U.S. patent application Ser. No. 10/305,620 filed Nov. 27, 2002, now U.S. Pat. No. 6,712,855 issued on Mar. 30, 2004. U.S. patent application Ser. No. 09/776,584 filed Feb. 2, 2001, now U.S. Pat. No. 6,508,841 issued on Jan. 21, 2003. U.S. patent application Ser. No. 09/003,061 filed Jan. 5, 1998, now U.S. Pat. No. 6,197,065 issued Mar. 6, 2001. U.S. patent application Ser. No. 08/535,532 filed Sep. 28, 1995, now abandoned. U.S. patent application Ser. No. 08/146,510 filed Nov. 1, 1993, now abandoned.

The disclosures of the above references are incorporated by reference herein.

FIELD

The present teachings relates to a hip bone prosthetic, and more particularly relates to a hip bone prosthetic that connects to the adjoining pubis bone with a sliding clamping member.

BACKGROUND

With reference to FIG. 1, a human pelvis is shown and generally indicated by reference numeral 10. The human pelvis 10 is comprised of a right and a left hemi-pelvis respectively indicated by reference numerals 12 and 14. The right and left hemi-pelvis 12 and 14 may also be referred to as a right and left hip bone 12 and 14, respectively. Mature hip bones 12 and 14 are each comprised of three principle bones fused together: An ilium 16, an ischium 18 and a pubis 20. The ilium 16 is the upper and the largest part of the pelvis and articulates on its inner aspect with a sacrum 22 at a sacroiliac joint 24. The ischium 18 is the more distal and posterior of the three principal bones of the pelvis 10 and may be commonly referred as a seat bone or a huckle bone. The pubis 20 is the more medial and anterior of the three principal bones of the pelvis 10 and may be commonly referred to as a share bone or a pubic bone.

The ilium 16, the ischium 18, and the pubis 20 are separated from each other by cartilage in young subjects (not shown) but are fused together as solid bone in a mature adult. The union of the ilium 16, the ischium 18, and the pubis 20 takes place, among other places, in and around a large cup-shaped articular cavity known as the acetabulum generally indicated by reference numeral 26. The acetabulum 26 is a hollow, cuplike portion of the hip bone 12 into which a head 28 of a femur 30 fits. The bone and muscle structure surrounding the head 28 of the femur 30 and the acetabulum 26 of the hip bone 12 allows for among other things the ability to walk.

It will be appreciated that there are muscles and associated connective tissue that retain the head 28 of the femur 30 within the acetabulum 26 and also provide for flexing and motion of the femur 30 relative to the hip bone 12. It will also be appreciated that while reference is made to either the hip bone 12, the discussion hitherto and throughout is applicable to hip bone 14.

The sacrum 22 is a triangular-shaped bone lying between the fifth lumbar vertebra (partially shown) and the coccyx (partially shown), which can be commonly referred to as the tailbone. The sacrum 22 consists of five vertebrae fused together and it articulates on each side with the respective ilia 16 to form sacroiliac joints 24. The sacrum 22, as well of as the other bones of the pelvis 10, may become damaged due to injury, or various medical conditions such as cancer, osteoporosis or various medical trauma, and as such may have to be partially removed and/or replaced in whole.

With reference to FIG. 2, the various medical conditions as mentioned above may deprive a patient of the acetabulum 26 of the hip bone 12 thereby necessitating a prosthetic to be implanted in its place. It will be appreciated that damage to the hip bone 12 can range from loss of use of one of the acetabulums 26 all the way to complete loss of one or both of the hip bones 12 and 14. If presented with a complete loss of one of the hip bone 12, it will be appreciated that a prosthetic hip bone or hemi-pelvis must be constructed to not only connect to the head 28 of the femur 30 but also connect to the opposing pubis bone 20a and the sacrum 22. If the hip bone 12 is not a complete loss it will be appreciated that the hip bone replacement must connect to the remaining portions of the hip bone 12 to otherwise restore complete functionality to the pelvis 10.

Hip prosthetics require bone screws and/or bone fusing material to establish a suitable connection to the remaining and healthy portions of the hip bone. Hip prosthetics also require bolts or bone screws threaded through brackets to connect to the remaining healthy bone. The additional hardware adds cost and complexity. The brackets further require that a larger area of the remaining healthy bone be exposed.

SUMMARY

The various embodiments of the present teachings include a prosthetic system for replacement of a portion of a hip bone including a plurality of acetabular components and a plurality of flange components. The prosthetic system also includes a plurality of pubis components. Each of the pubis components and each of the flange components are operable to connect to each of the acetabular components. Each of the pubis components define a clamping portion that is configured to attach to an opposed healthy pubis bone. An angle between the flange component and the pubis component varies among the acetabular components.

The present teachings provide a prosthetic device for replacement of a first pelvic portion of a pelvis of a patient opposite to a second pelvic portion relative to a median plane includes an acetabular component a flange component and a pubis component. The acetabular component has a first connecting portion and a second connecting portion at an angle relative to the first connecting portion, the angle selected for a corresponding anatomy of the patient. The flange component is coupled to the first connecting portion and configured to attach to a healthy pelvic portion on a same side of the median plane from the first pelvic portion. The pubis component is connected to the second connecting portion of the acetabular component and having a clamping portion configured to attach to a healthy pubis bone on an opposite side of the median plane from the first pelvic portion.

The present teachings also provide a method of replacing a first pelvic portion of a pelvis of a patient opposite to a second pelvic portion relative to a median plane with a prosthetic device. The method includes providing a prosthetic device constructed by imaging of the first and second pelvic portions and resecting a part of the first pelvic portion such that connective tissues are still attached to a remainder of the first pelvic portion. The method includes forming anatomical connection points on the prosthetic device to substantially match the remainder of the first pelvic portion, connecting the prosthetic device to the remainder of the first pelvic portion at the connecting points, and connecting a pubis member of the prosthetic device to an opposed pubis bone of the pelvic portion.

Further areas of applicability of the present teachings will become apparent from the detailed description provided hereinafter. It should be understood that the detailed description and specific examples, while indicating the various embodiments of the present teachings, are intended for purposes of illustration only and are not intended to limit the scope of the teachings.

BRIEF DESCRIPTION OF THE DRAWINGS

The present teachings will become more fully understood from the detailed description, the appended claims, and the accompanying drawings, wherein:

FIG. 1 is a partial front view of a human pelvis that includes two opposed hip bones each having an ilium, an ischium, and a pubis fused together to form an acetabulum, the acetabulum accepts a head of a femur;

FIG. 2 is a partial front view of the human pelvis of FIG. 1 showing one of the hip bones partially resected;

FIG. 3 is a partial front view of the human pelvis of FIG. 1 showing one of the hip bones completely resected;

FIG. 23 is an exploded assembly view of an alternative configuration of partial hip prosthetic with modular components including a pubis clamp component, a hip flange component and an acetabular component in accordance with the various embodiments of the present teachings;

FIG. 24 is similar to FIG. 23 and shows the partial hip prosthetic assembled;

FIG. 34 is similar to FIG. 25 and shows the pubis clamp of FIG. 29; and

FIG. 35 is similar to FIG. 25 and shows the pubis clamp of FIG. 32.

DETAILED DESCRIPTION OF THE VARIOUS EMBODIMENTS

The following description of the various embodiments is merely exemplary in nature and is in no way intended to limit the teachings, its application, or uses. While the illustrated embodiments pertain to one hip bone or hip bone of the human body, it will be appreciated that the present teachings is applicable to the bones of the pelvis of any creature and further is applicable to either the right or the left hip bone.

Figure 4:
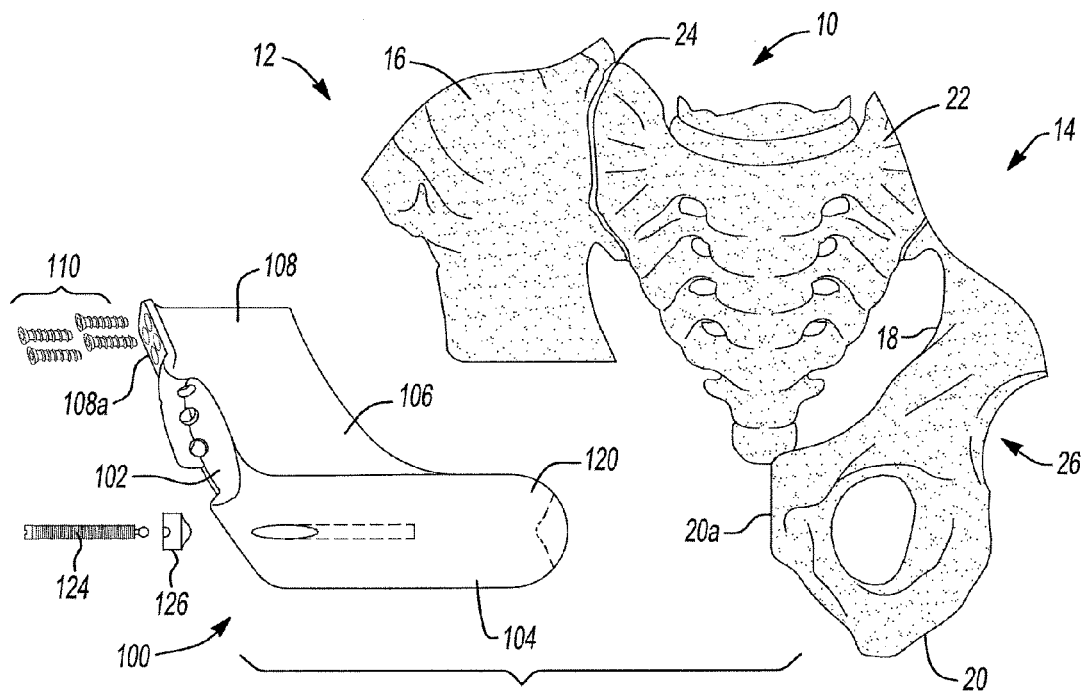
FIG. 4 is a partial front view of a pelvis showing a partial hip prosthetic constructed in accordance with the various embodiments of the present teachings.
Figure 5:
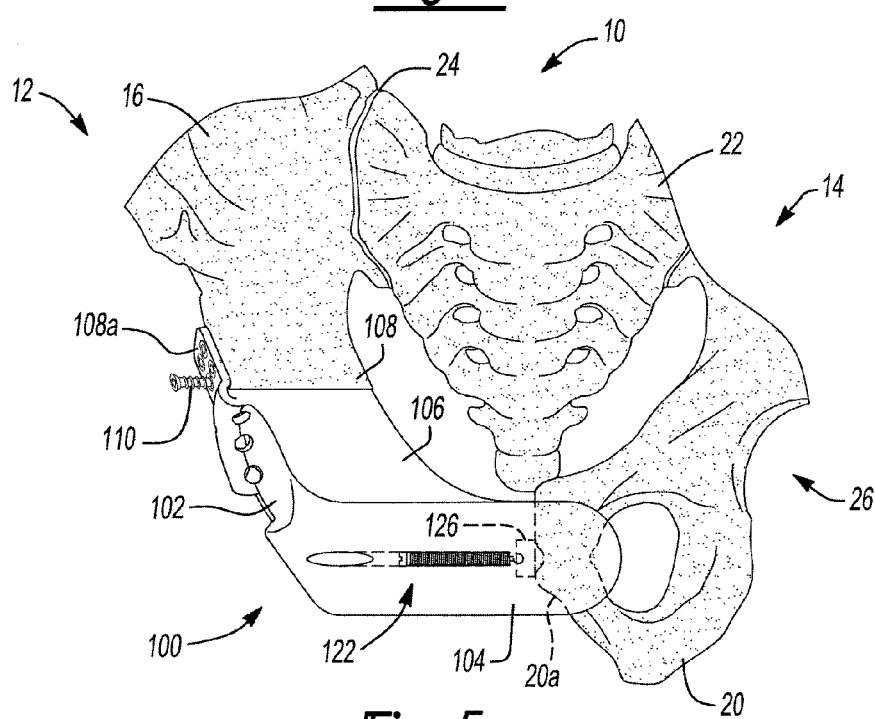
FIG. 5 is a partial front view of the pelvis showing the partial hip prosthetic of FIG. 4 connected to remaining healthy portions of the pelvis.
Figure 6:
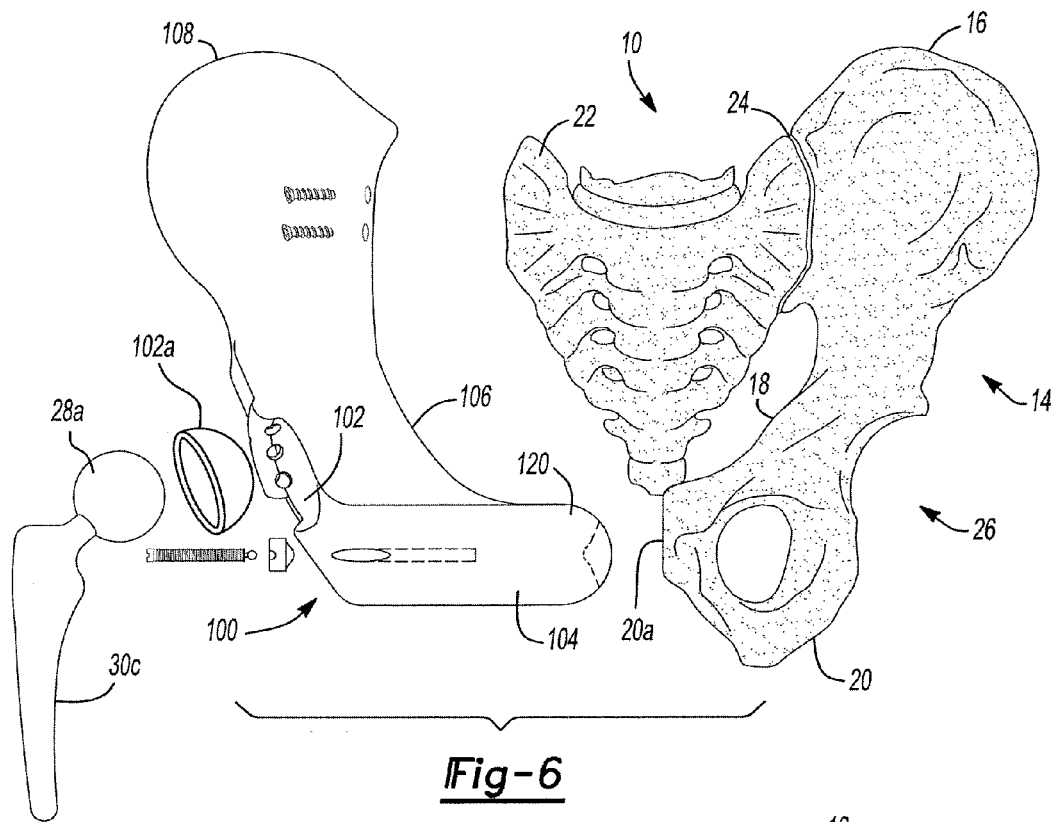
FIG. 6 is a partial front view of the pelvis showing a complete hip bone prosthetic replacement with a acetabular liner and a femoral component constructed in accordance with the various embodiments of the present teachings.
Figure 10:
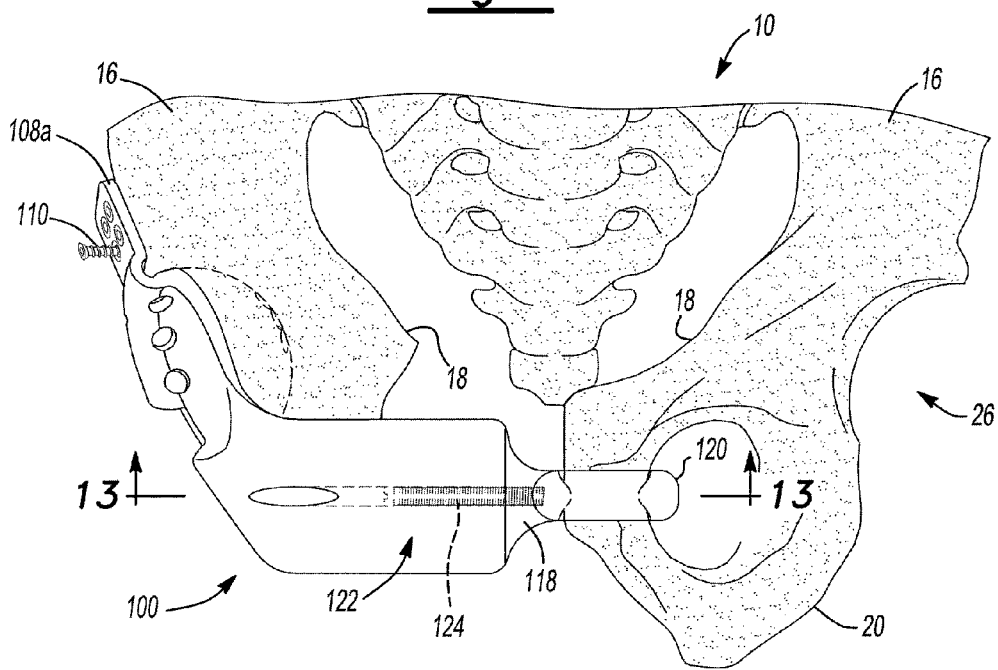
FIG. 10 is a partial front view of the pelvis showing the partial hip prosthetic of FIG. 9 connected to the remaining healthy portions of the healthy pelvis.

With reference to FIGS. 4-10, a hip prosthetic is generally indicated by reference numeral 100. In the various embodiments, the hip prosthetic 100 replaces all of or a portion of one of the hip bone's 12 of the pelvis 10. The hip prosthetic 100 includes an acetabular component 102 connected with a pubis member 104, an ischium member 106, and an ilium member 108. It will be appreciated that as more of a damaged hip bone 12 is removed due to various medical concerns, the replacement hip prosthetic 100 can be sized accordingly to otherwise replace a completely removed hip bone 12, as shown in FIG. 6. In FIGS. 5 and 10, for example, portions of the hip bone 12 remain after resection so that the hip prosthetic 100 is sized to connect to remaining and healthy portions of the hip bone 12. It will be appreciated portions of the hip bone prosthetic or connectors used therewith can be sized and configured accordingly to produce a kit of modular of components.

The acetabular component 102 is configured to mimic the acetabulum 26 of a healthy hip bone 12, as shown in FIG. 1. Similar to one of the hip bone 12, the acetabular component 102 is formed around the interconnection of the pubis member 104, the ischium member 106 and the ilium member 108.

In the various embodiments, the acetabular component 102 is sized to mate with a femoral component 30c that serves as, among other things, a prosthetic head 28a to the femur 30, as shown in FIG. 6. As such, the joint between the femur 30 and the hip bone 12 can be comprised of artificial components and/or one or more bushings or liners made of suitable metals, plastics or ceramics.

The acetabular component 102 can be configured as an acetabular cup to accept a prosthetic femoral head 28a of the femoral component 30c. It will be appreciated that the acetabular component 102 can also be configured to receive an acetabular cup, such that the acetabular cup can be positioned and seated in the acetabular component 102 and secured with suitable bone cement or other suitable fasteners. It will be additionally appreciated that additional liners 102a or bushings may be included in the acetabular component 102 to further facilitate the junction between the acetabular component 102 and the prosthetic femoral head 28a. More specifically, the prosthetic femoral head 28a can be attached to the acetabular component 102 using, for example, ring locks, or taper junctions. Furthermore, the acetabular component 102 can be configured to accept the natural femoral head 28. In this instance, additional liners 102a and/or bushing can be used to facilitate the junction between the acetabular component 102 and the natural femoral head 28.

Figure 11:
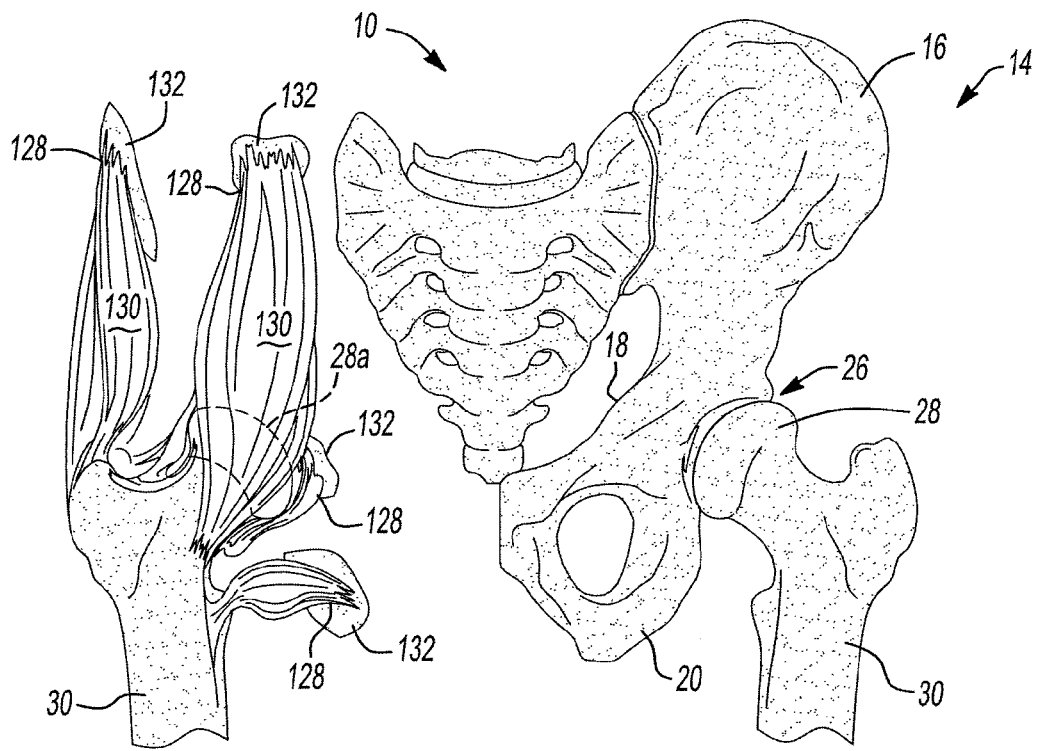
FIG. 11 is a partial front view of the pelvis with one of the hip bones partially resected leaving a plurality of bone portions attached to the associated connective tissue in preparation for reattachment of the plurality of bone portions to the prepared hip bone prosthetic.

The ilium member 108 and the ischium member 106 can be configured to otherwise mimic the natural configuration of the hip bone 12 (FIG. 1). More specifically, a patient receiving the hip prosthetic 100 can be examined before the hip replacement surgery so that the hip prosthetic 100 can be configured to be generally identical to the portions of the hip bone 12 that the hip prosthetic replaces. It will be appreciated that if the hip bone 12 is completely removed, as shown in FIG. 6, that the hip prosthetic 100 must connect directly to the sacrum 22 as opposed to connecting to the remaining healthy portions of the hip bone 12. It will also be appreciated that portions of the otherwise healthy ilium 16 or ischium 18 can be resected from the patient and attached to portions of the hip prosthetic 100 to further serve in expediting the rehabilitation process, as shown in FIG. 11. This process will be discussed in greater detail below.

Figure 7:
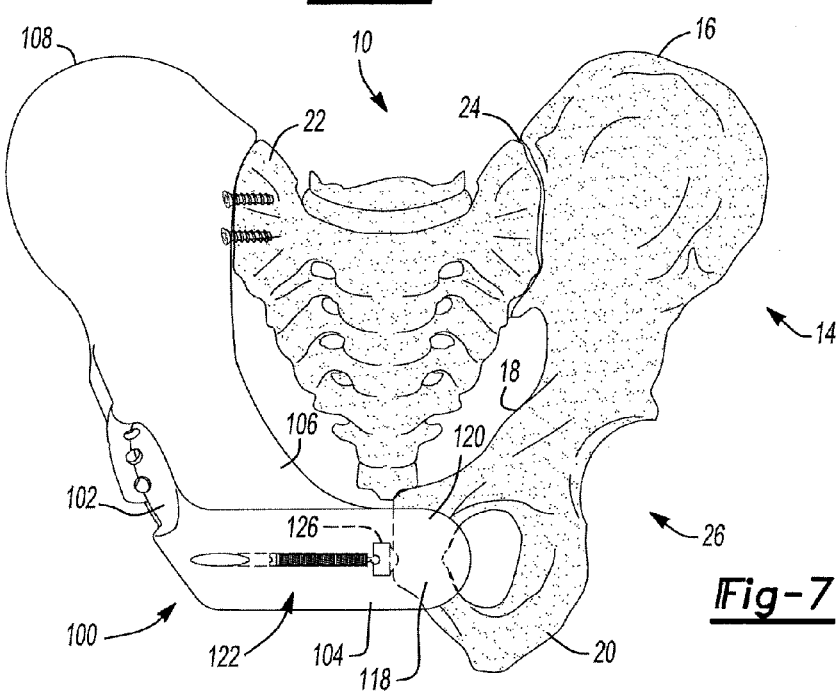
FIG. 7 is a partial front view of the pelvis showing the complete hip prosthetic of FIG. 6 connected to the remaining healthy portions of the pelvis.
Figure 8A:
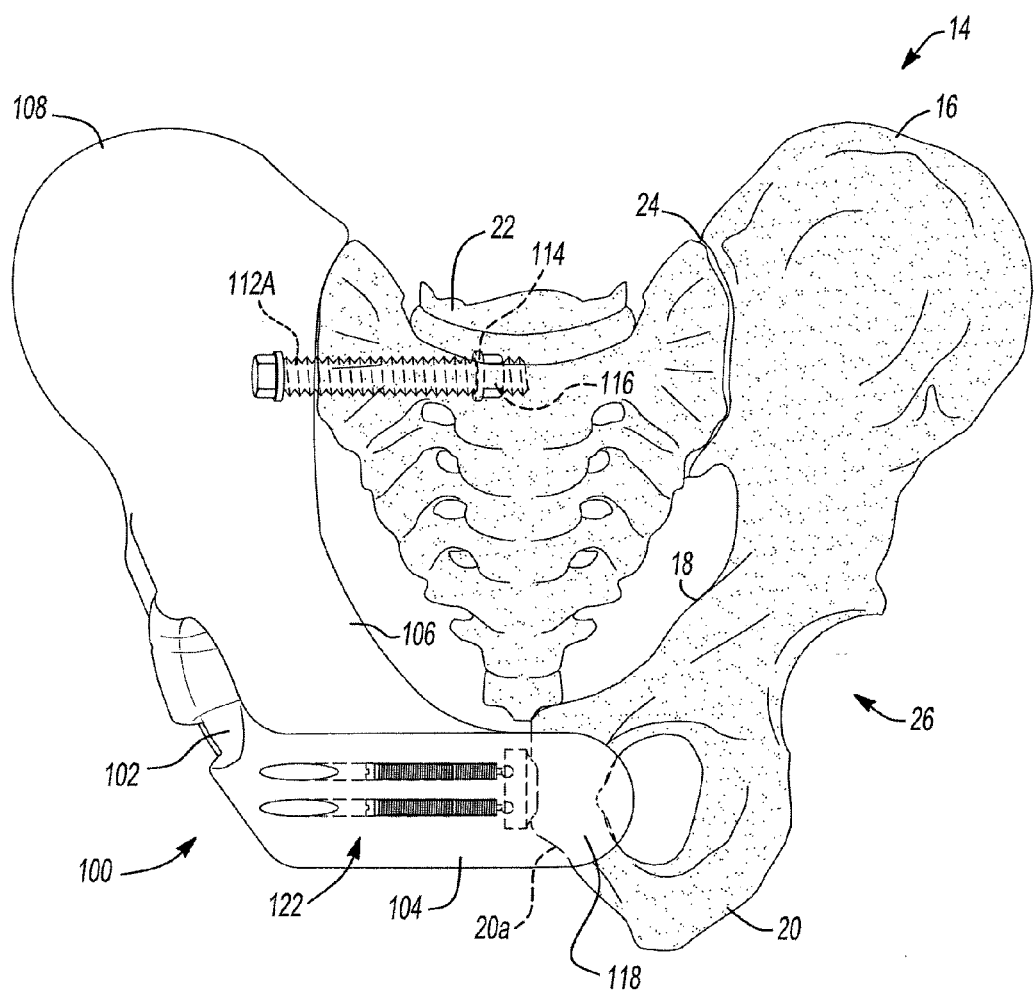
FIG. 8A is a partial front view of the pelvis showing the complete hip bone prosthetic replacement of FIG. 7 with an alternative fastener between the complete hip prosthetic and a sacrum and an alternative configuration of a worm drive constructed in accordance with the various embodiments of the present teachings.
Figure 8B:
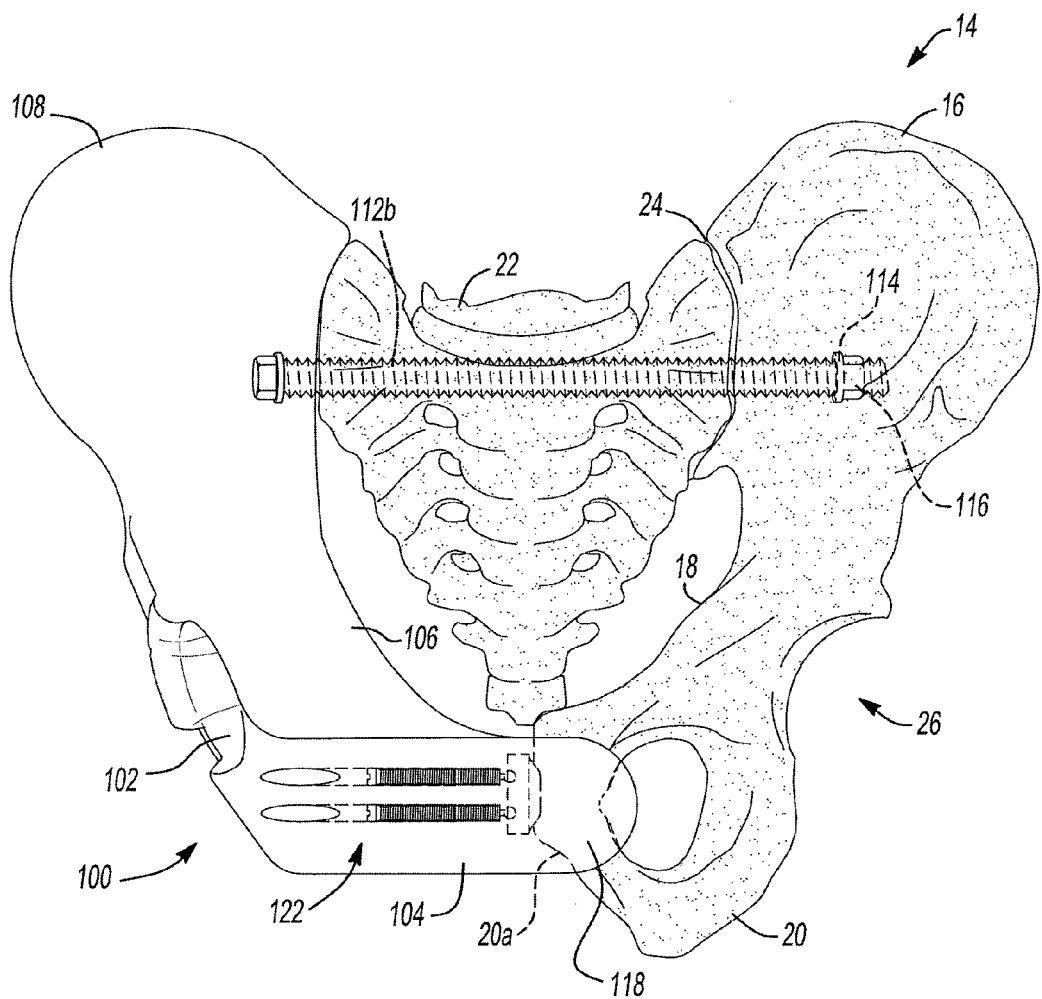
FIG. 8B is a partial front view of the pelvis showing the complete hip bone prosthetic replacement of FIG. 7 with an alternative fastener between the complete hip prosthetic, a sacrum, and the healthy hip bone.
Figure 9:
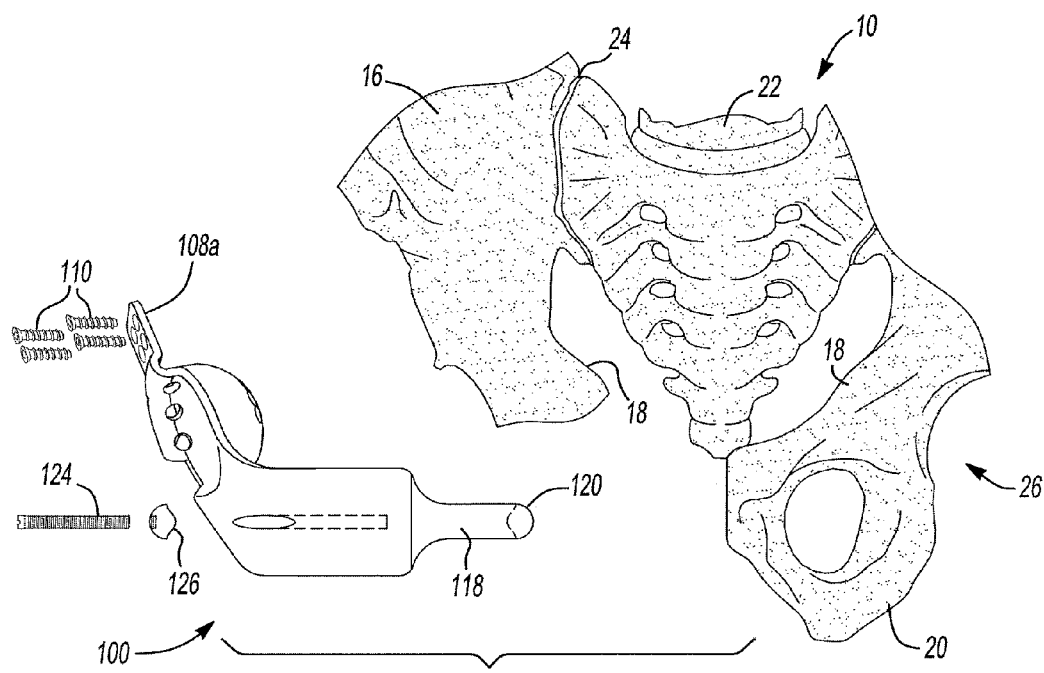
FIG. 9 is a partial front view of the pelvis showing an alternative partial hip prosthetic constructed in accordance with the various embodiments of the present teachings.

If the hip bone 12 is completely removed and the hip prosthetic 100 must serve as essentially a new hip bone 12, the ilium member 108 of the hip prosthetic 100 can be configured to connect directly to the sacrum 22. Connection to the sacrum 22 can be accomplished by driving suitable bone screws 110 through portions of the ilium member 108 and through portions of the sacrum 22 to connect thereto, as shown in FIG. 7. In the various embodiments, a suitable bolt 112 can also be used such that one or more holes are drilled in the ilium member 108 and in the sacrum 22, as shown in FIG. 8A, and through the sacrum 22 into the opposed ilium member 16, as shown in FIG. 8B. A bolt 112A is passed through the ilium member 108 and into the sacrum 22 and is connected thereto with the washers 114 and fasteners 116, as shown in FIG. 8A. In FIG. 8B, a bolt 112B is passed through the ilium member 108 and the sacrum 22 to the healthy ilium 16 and is connected thereto with the washers 114 and fasteners 116, thereby pulling the ilium member 108 in close contact with the sacrum 22 and ilium 16.

In the various embodiments when the hip bone 12 is not completely removed, the ilium member 108 of the hip prosthetic 100 can be connected to the remaining healthy portion of the ilium 16. As shown in FIGS. 4 and 5, portions of the healthy hip bone 12 may remain while portions of the damaged bone are resected. In this case, the pubis member 104, the ilium member 108 and the ischium member 106 of the hip prosthetic 100 can be configured to connect to the remaining healthy portions of the otherwise healthy hip bone 12.

In the various embodiments, a connecting flange 108a can be configured to engage the remaining healthy portions of the hip bone 12. Bone screws 110 can be driven though the connecting flange 108a and into the hip bone 12 to secure the prosthetic hip 100. It will be appreciated that the connecting flange 108a can be connected to the ilium member 108 of the prosthetic hip 100 to engage the remaining portion of the ilium 16. The connecting flange 108a can also be located at other locations on the prosthetic hip 100 to facilitate connection to other portions of the pelvis 10 with bone screws 100 or other suitable fasteners such as bone cement or a porous material to promote bone growth into the connecting flange 108a.

The pubis member 104 of the hip prosthetic 100 is connected to the acetabular component 102 and also serves as a connection to the opposed healthy pubis bone 20a of the healthy hip bone 14. The pubis member 104 includes a connecting member 118 that connects the acetabular component 102 to a clamping portion 120. The clamping portion 120 includes a worm drive generally indicated by reference number 122. The worm drive 122 includes one or more threaded rods 124 that are attached to a catch plate 126 that is driven against the opposed pubis bone 20a of the opposite healthy hip bone 14. When the catch plate 126 is driven against the pubis bone 20a, the clamping portion 120 is drawn from the side opposite the catch plate 126 thereby clamping the opposed pubis bone 20a between the catch plate 126 and the clamping portion 120.

Figure 14:
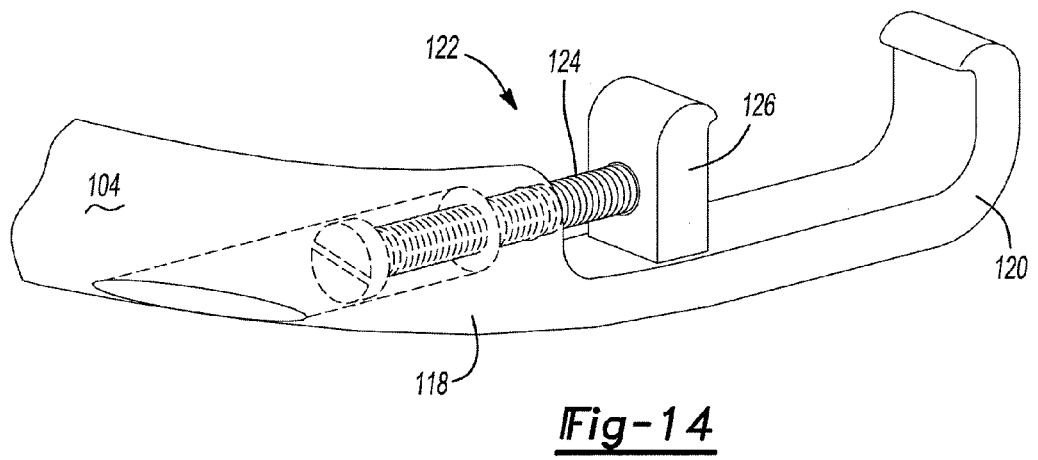
FIG. 14 is a partial perspective view of FIG. 13 showing the pubis member including the worm drive, a catch plate and the clamping portion.
Figure 16:
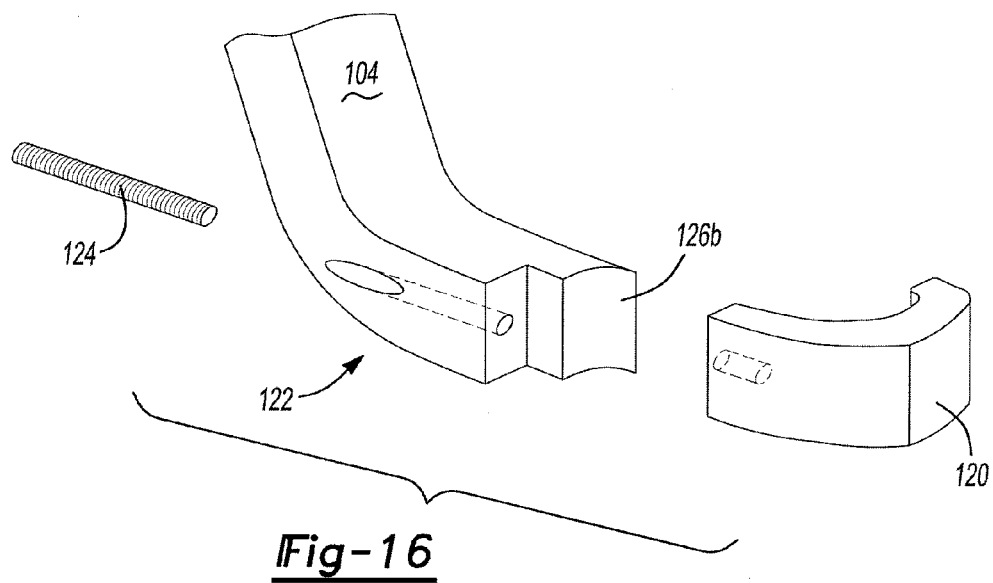
FIG. 16 is a partial perspective view of the pubis member configured with an alternative clamping portion constructed in accordance with the various embodiments of the present teachings.

The worm drive 122 of the clamping portion 120 is configured with the pubis member 104 so that the clamping portion 120 can simply be tightened by rotating the worm drive 122. Various configurations of the catch plate 126, as shown in FIGS. 14 and 16, and multiple worm drives 122, as shown in FIG. 8, can be used to further connect and stabilize the clamping portion 120 to the opposed hip bone 14. It will further be appreciated that multiple catch plates 126 and various configurations of the clamping portion 120 can be used and that each of the catch plates 126 can be further configured to compliment the shape of the opposed pubis bone 20a to which it contacts. It will additionally be appreciated that multiple worm drives 122 can be used with a single catch plate 126 or multiple catch plates 126 to further facilitate connection to the pubis bone 20a.

Figure 15:
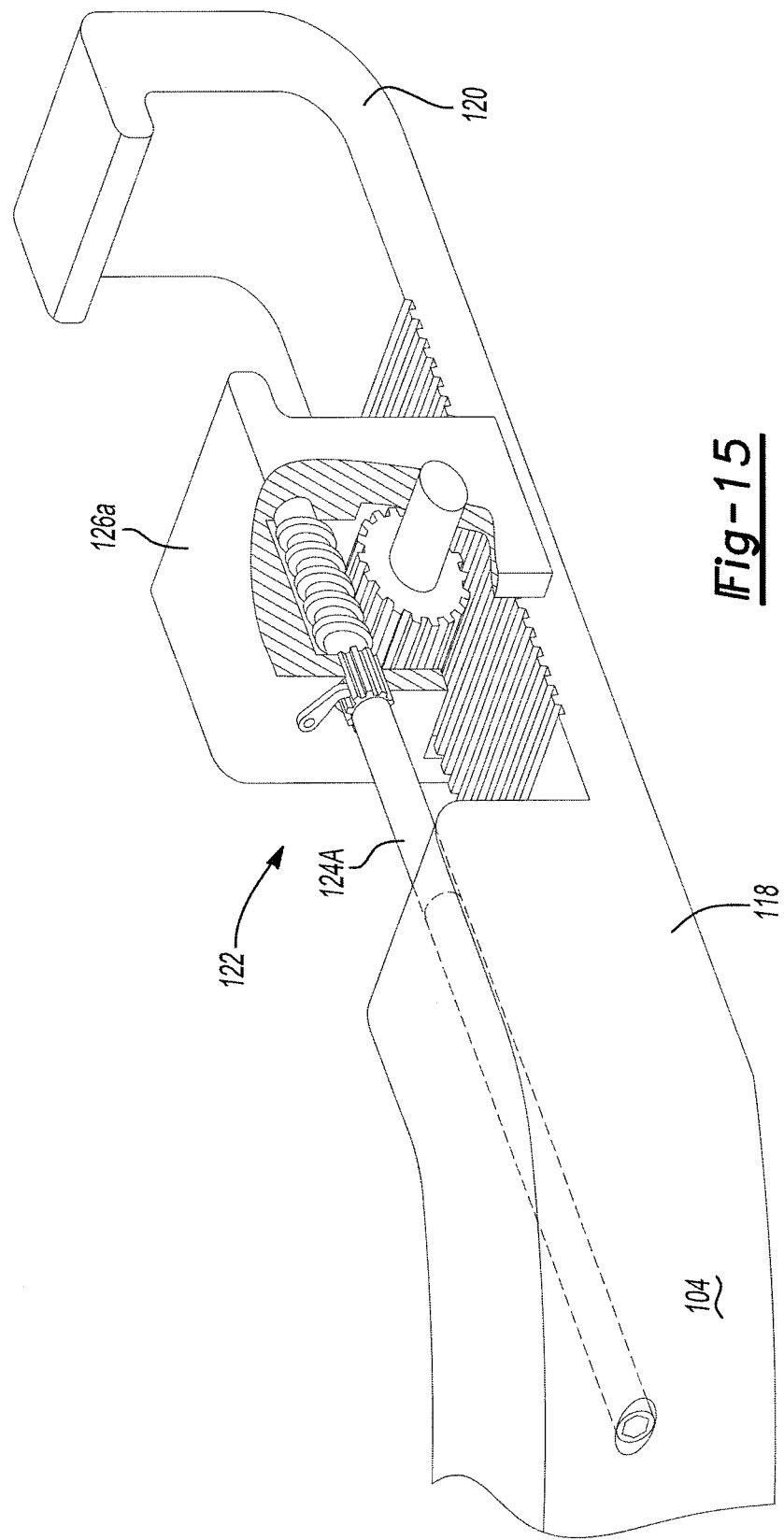
FIG. 15 is a partial perspective view of the pubis member configured with an alternative clamping portion having a ratcheting worm drive constructed in accordance with the various embodiments of the present teachings.

With specific reference to FIG. 15, the clamping portion 120 and catch plate 126 can be configured so that the catch plate ratchets and slides toward the clamping portion 120. Rotation of a partially threaded rod 124a drives the catch plate 126. A catch plate ratchet 126a can be configured to ratchet closed and open by releasing the ratchet. The opposite is also possible.

With specific reference to FIG. 16, the clamping portion 120 can be configured so that the catch plate 126b is fixed and the clamping portion 120 is drawn toward the pubis member 104 when the worm drive 122 is rotated. The catch plate 126b can be configured as an integral portion or movably connected thereto. In the various embodiments, the clamping portion 120 can be a single clamp or be configured with multiple clamping portions 120 driven by multiple worm drives 122. Further, a single clamping portion 120 may be driven by multiple worm drives 122 to further facilitate stabilization of the pubis member 104.

Figure 17:
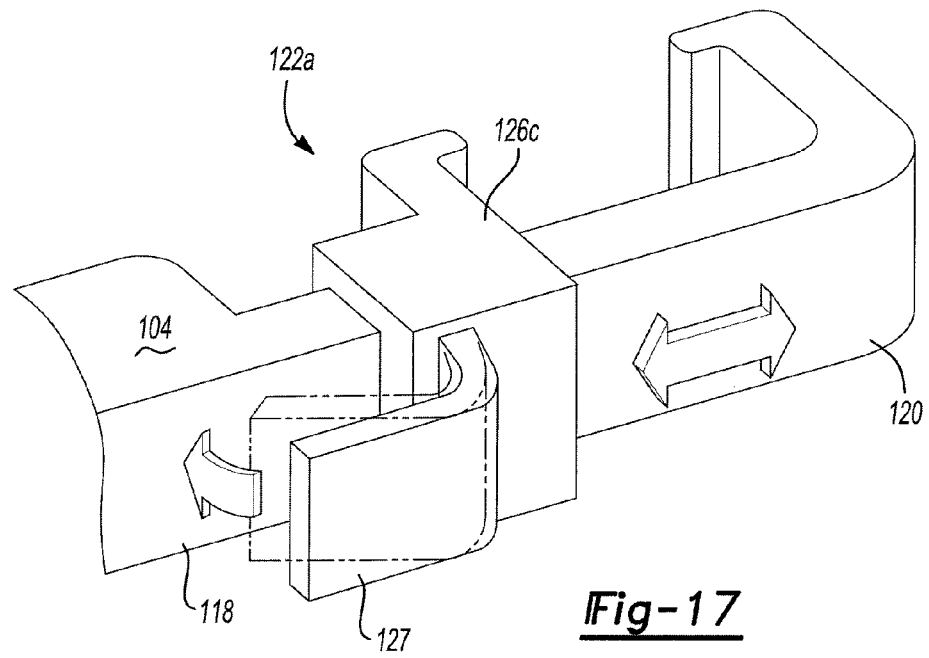
FIG. 17 is a partial perspective view of the pubis member configured with an alternative clamping portion having a spring lever constructed in accordance with the various embodiments of the present teachings.

With specific reference to FIG. 17, the clamping portion 120 can be configured so that the catch plate 126c contains a spring clamp 127. The catch plate 126c is advanced toward or can retreat from the clamping portion 120 when the spring clamp 127 is released. In the various embodiments, the clamping portion 120 can be a single clamp or be configured with multiple clamping portions 120.

Figure 18:
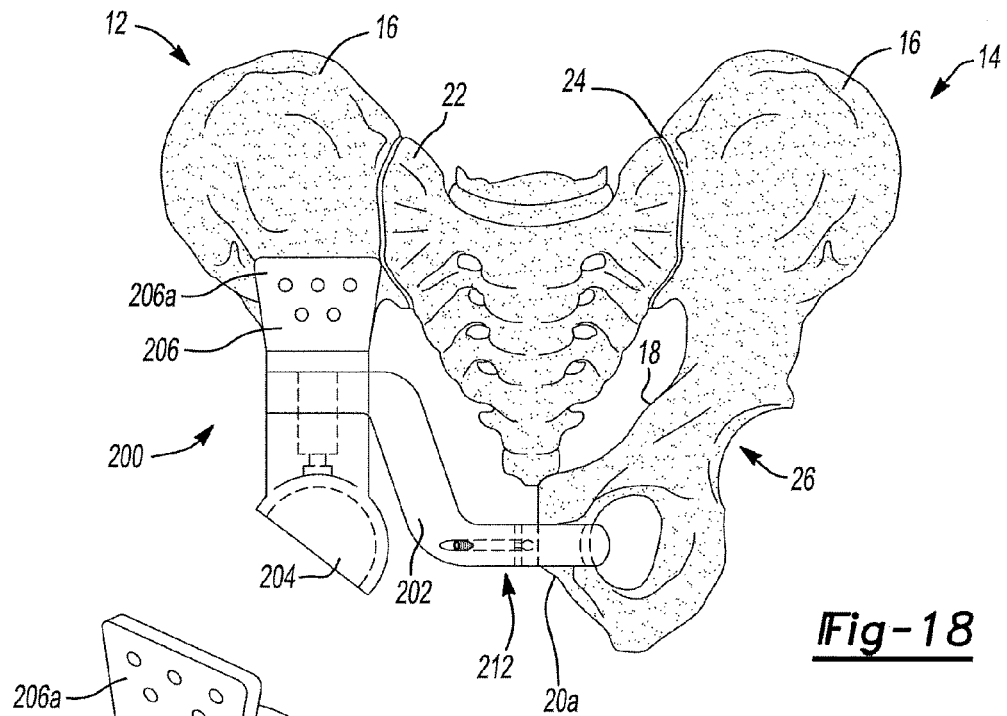
FIG. 18 is a front view of the pelvis showing an alternative configuration of the partial hip prosthetic with modular components including a pubic clamp component, a hip flange component, and a acetabular component constructed in accordance with the various embodiments of the present teachings.
Figure 19:
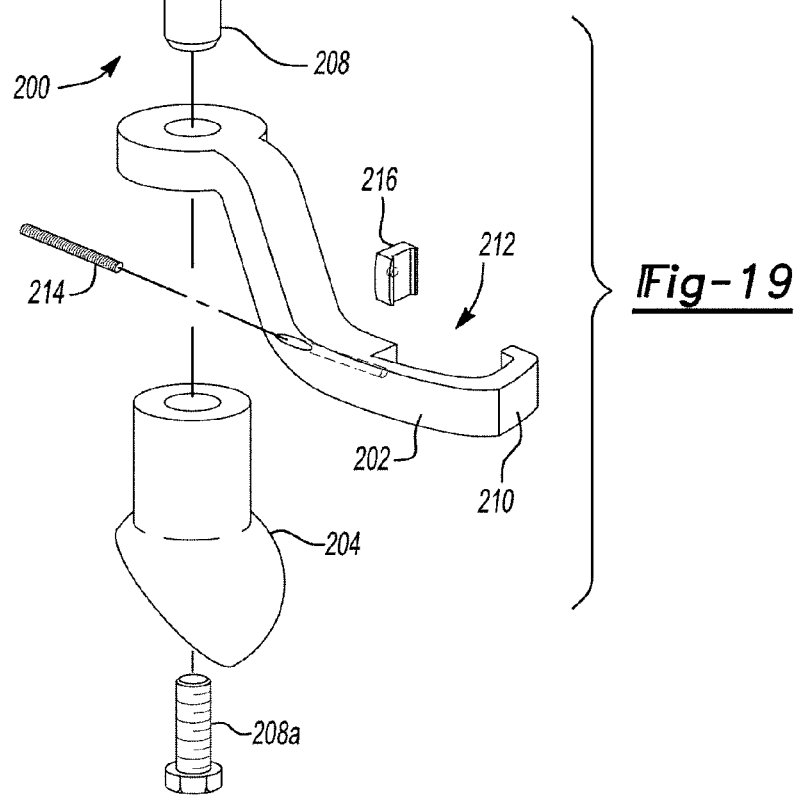
FIG. 19 is an exploded perspective view of the partial hip prosthetic of FIG. 16 showing the public clamp component including a worm drive and a clamping portion.

With reference to FIGS. 18 and 19, the hip prosthetic 100 can also be made of a modular multi-component construction generally indicated by reference numeral 200. The modular prosthetic hip 200 includes a pubis clamp component 202, an acetabular component 204, and a hip flange component 206. The hip flange component 206 includes an assembly rod 208 that is inserted through the pubis clamp component 202 through to the acetabular component 204 and held together with an assembly rod fastener 208a. Because the pubis clamp component 202 is inserted over the assembly rod 208 it can move relative to the acetabular component 204. It will also be appreciated that the various components of the modular prosthetic hip 200 can be passed into the surgical area piece by piece and assembled in the surgical area, thus providing a less invasive technique.

In the various embodiments, a connecting flange 206a can be configured to engage the remaining healthy portions of the hip bone. Bone screws 110 (FIG. 9) can be driven though the connecting flange 206a and into the hip bone 12 to secure the modular prosthetic hip 200. It will be appreciated that the connecting flange 206a can be connected to the hip flange component 206 in various positions and locations to engage the remaining portion of the ilium 16 or other portions of the pelvis 10. The connecting flange 206a can also be configured in a cup-like bow-like fashion to further facilitate connection of the modular prosthetic hip 200 to other portions of the pelvis 10. The connecting flange 206a can be connected to portions of the pelvis with bone screws 100 or other suitable fasteners such as bone cement or a porous material to promote bone growth into the connecting flange 108a.

The acetabular component 204 can be configured as an acetabular cup to accept a prosthetic femoral head 28a of the femoral component 30c (FIG. 6). It will be appreciated that the acetabular component 204 can be configured to receive an acetabular cup, such that the acetabular cup can be positioned and seated in the acetabular component 204 and secured with suitable bone cement or other suitable fasteners. It will be additionally appreciated that additional liners 102a (FIG. 6) or bushings may be included in the acetabular component 204 to further facilitate the junction between the acetabular component 204 and the prosthetic femoral head 28a. More specifically, the prosthetic femoral head 28a can be attached to the acetabular component 204 using, for example, ring locks, or taper junctions. Furthermore, the acetabular component 204 can be configured to accept the natural femoral head 28. In this instance, additional liners 102a and/or bushing can be used to facilitate the junction between the acetabular component 204 and the natural femoral head 28.

A clamping portion 210 of the pubis clamp component 202 is similar to that of the clamping portion 120, as shown in FIG. 14. As such, the pubis clamp component 202 includes a worm drive generally indicated by reference numeral 212. The worm drive 212 includes a threaded rod 214 threaded through the pubis clamp component 202. The threaded rod 214 connects to a catch plate 216. Rotating the worm drive 212 tightens the catch plate 216 against the pubis bone 20a and draws the pubis clamp component 202 closer to the catch plate 216, thus securing the pubis bone 20a in the pubis clamp component 202.

The worm drive 212 can also be configured such that one or more of the threaded rods 214 are attached to one or more of the catch plates 216, which further facilitate holding the pubis bone 20a in the pubis clamp component 202. It will be appreciated that various sizes of the catch plates 216 and the multiple worm drives 212, as illustrated in FIG. 8, can be used to further connect and stabilize the pubis clamping component 202 to the opposed pubis bone 20a. It will further be appreciated that the catch plates 216 can be further configured to compliment the shape of the opposed pubis bone 20a. It will be additionally appreciated that multiple worm drives 212 can be used with a single catch plate 216 or multiple catch plates 216 to further facilitate connection to the pubis bone 20a.

It will also be appreciated, that the pubis clamp component 202 can be configured so that the catch plate 216 is fixed and the clamping portion 210 is drawn toward the assembly rod 208 when the worm drive 212 is rotated, similar to that of FIG. 15. The fixed catch plate 216 is configured as an integral portion of the pubis clamp component 202 and the clamping portion 210 is attached to worm drive 212, such that the clamping portion 120 can be driven away from or toward the assembly rod 208 upon rotation of the worm drive 212. As with other various embodiments of the present teachings, the clamping portion 210 can be a single clamp or be configured with multiple clamping portions 210 driven by multiple worm drives 212. Further, a single clamping portion 210 may be driven by multiple worm drives 212 to further facilitate stabilization of the pubis clamp component 202. In addition, the clamping portion 210 and the catch plate can be configured with the functionality from the catch plate ratchet 216 (FIG. 15) and the spring lever 127 (FIG. 17).

Figure 20:
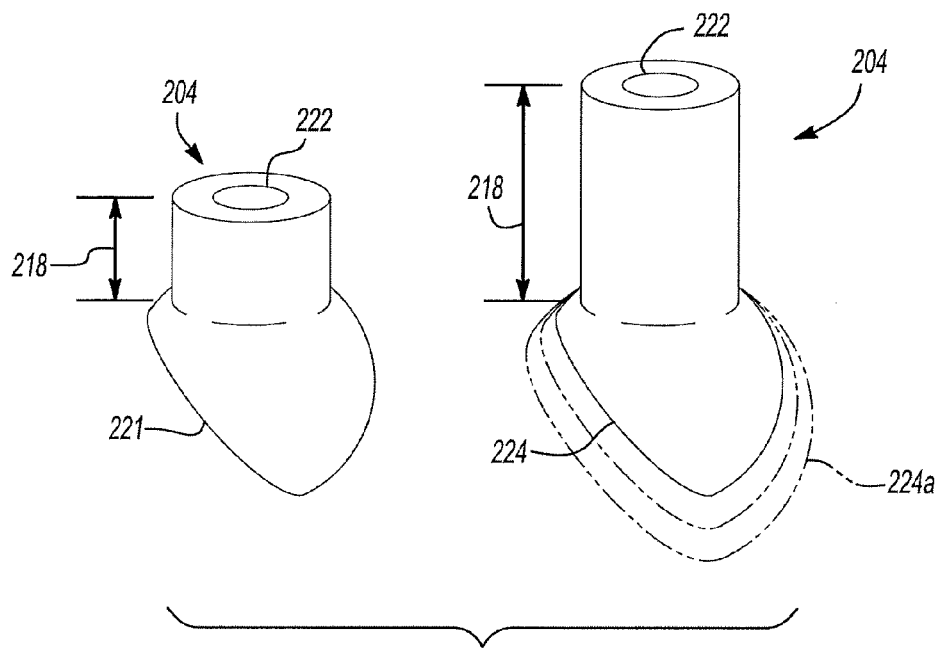
FIG. 20 is a perspective view of the acetabular component of FIG. 16 illustrating various configurations of the acetabular component constructed in accordance with the various embodiments of the present teachings.
Figure 21:
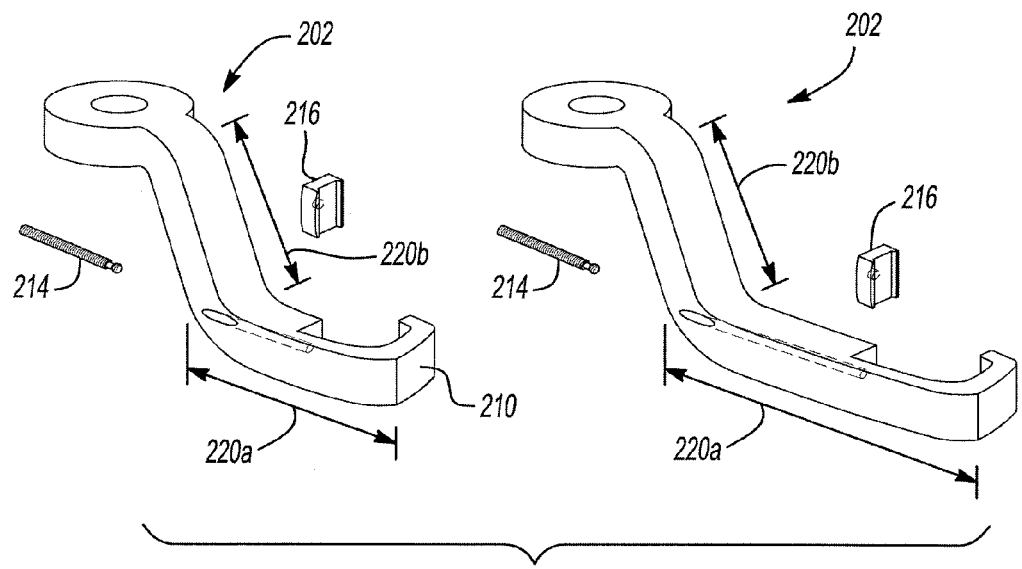
FIG. 21 is a perspective view of the acetabular component of FIG. 16 illustrating various configurations of the pubic clamp component constructed in accordance with the various embodiments of the present teachings.

With reference to FIGS. 20 and 21, it will be appreciated that the various components of the modular prosthetic hip 200 can be sized based on the size of the remaining portions of the pelvis 10 (FIG. 1) and other restrictions that can exist in the operating area. As such, the acetabular component 204 can be configured in different sizes, all of which can be available to the doctor during surgery. An acetabular neck length 218 and clamping portion lengths 220a and 220b can vary based on, among other things, the patient's anatomy. It will be appreciated that an aperture 222 on the acetabular component can also be recessed further in the acetabular component 204 to adjust positioning and length. For example, the female pelvis is smaller than the male pelvis, and furthermore the pelvis of a child is smaller than that of an adult. Because of the varying sizes required, the modular prosthetic hip 200 can be provided in many different sizes. The modular prosthetic hip 200 can also be configured to connect to a prosthetic femoral component, and as such, an acetabular cup 224 can be fabricated in various sizes 224a to fit the various modular femoral components available.

Figure 12:
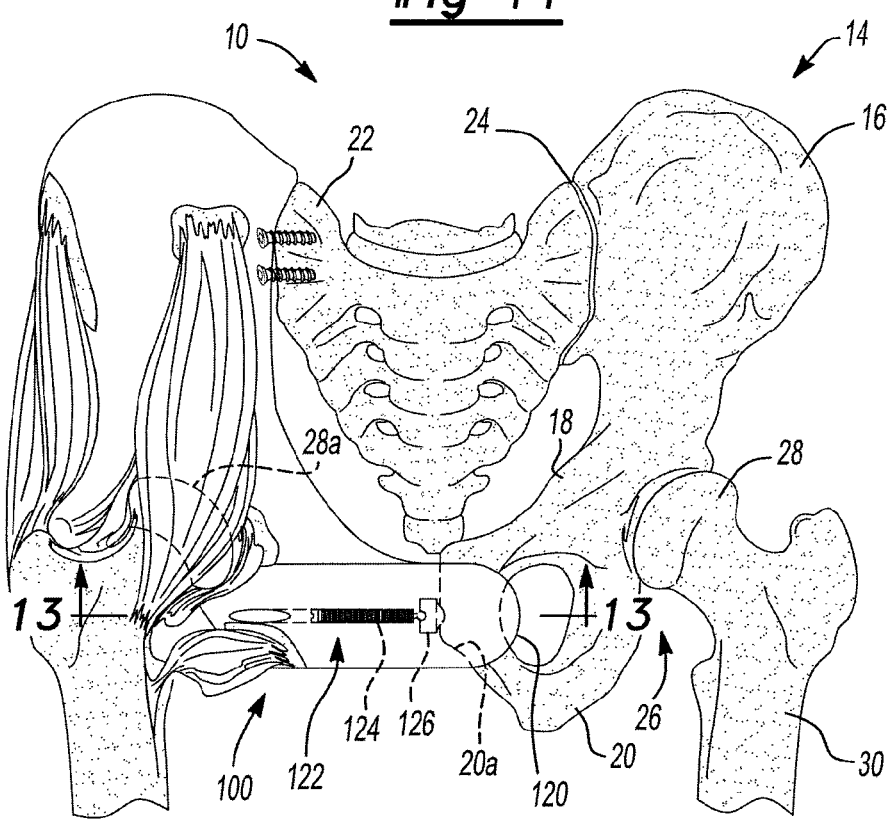
FIG. 12 is a partial front view of the pelvis of FIG. 11 showing the complete hip prosthetic connected to the plurality of bone portions attached to the associated connective tissue and also secured to the sacrum and the opposed healthy pubis bone.
Figure 13:
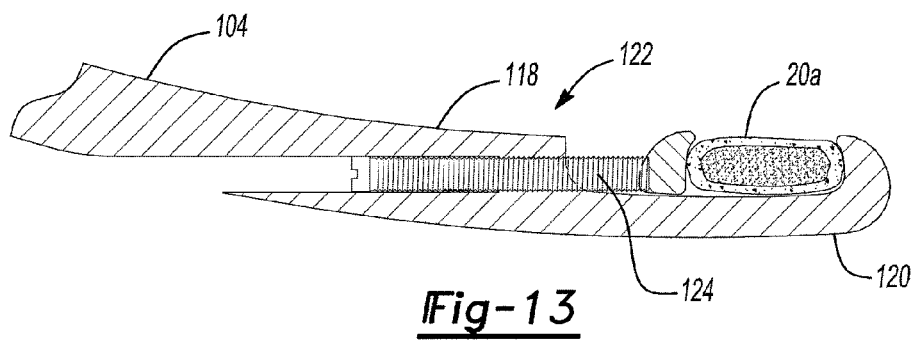
FIG. 13 is a cross section view from FIGS. 10 and 12 showing a pubis member of the hip prosthetic having a clamping portion and the worm drive that clamps the opposed healthy pubis bone to the pubis member of the hip prosthetic replacement constructed in accordance with the teachings of the present teachings.
Figure 22:
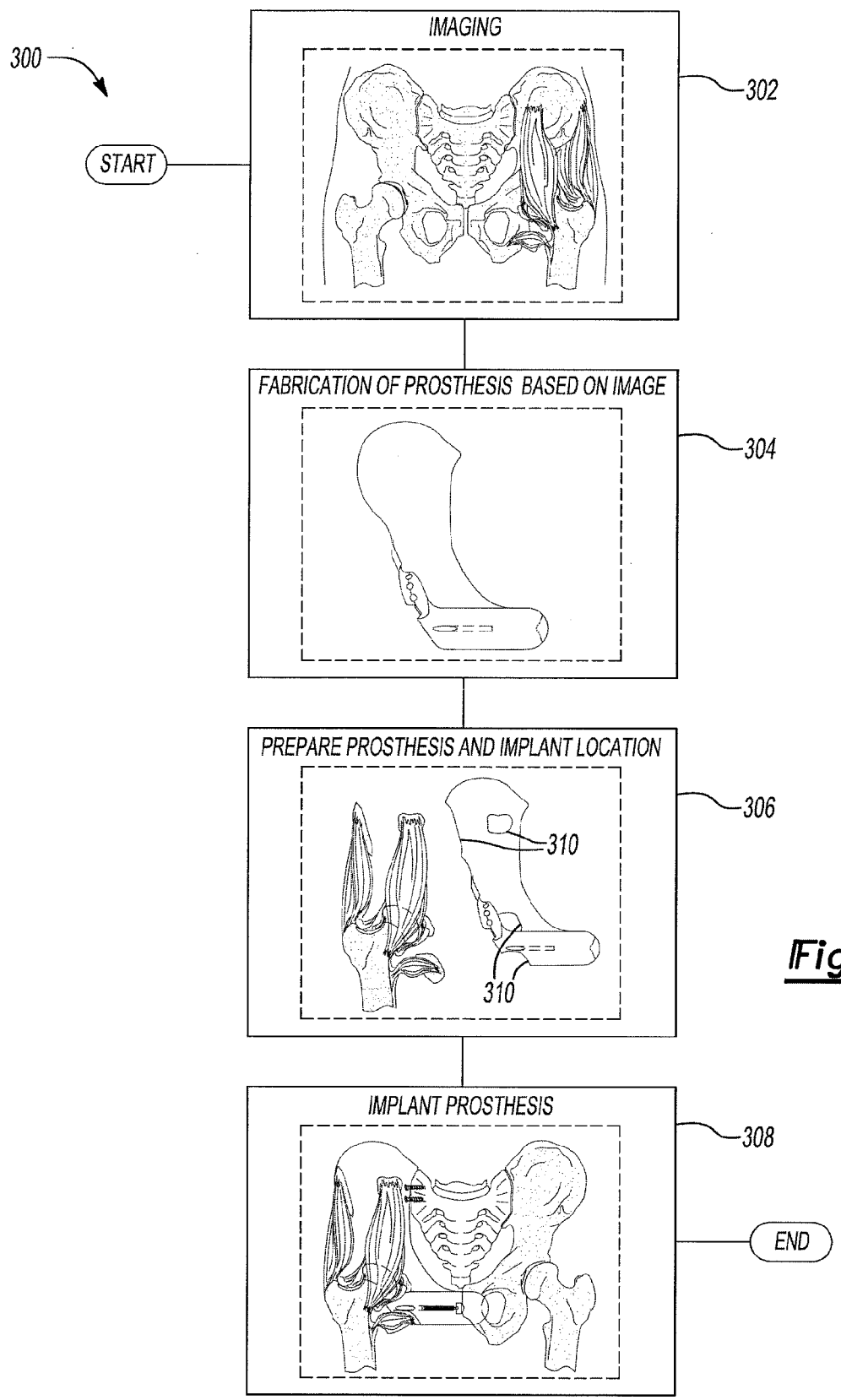
FIG. 22 is a flowchart illustrating a method of fabricating and implanting the hip prosthetic based on imaging of portions of the healthy pelvis.

With reference to FIGS. 1, 12, and 22, a method of using the hip prosthetic 100 is generally indicated by reference numeral 300. In block 302, a patient's healthy pelvis is imaged by a suitable imaging system to produce three-dimensional information of the patient's healthy pelvis. An exemplary suitable imaging machine can be, but is not limited to, a computed tomography (CT) imaging system or a Computed Axial Tomography (CAT) imaging system. It will be appreciated that the three dimensional data may be obtained either from the pelvis 10 or specifically from the hip bone 12, which is the hip bone that is to be replaced.

In some instances, however, the hip bone 12 may be so damaged for various reasons such that imaging of the hip bone 12 would be impractical. In this instance, the three-dimensional information can be obtained from the remaining healthy portions of the pelvis 10 and specifically from the opposed healthy hip bone 14. If the hip bone 14 is imaged to obtain three-dimensional information for the fabrication of the hip prosthetic 100, which will replace the hip bone 12, the three-dimensional information can be converted so that it can be used to re-create the prosthetic version of the hip bone 12.

As stated earlier, it will be appreciated that replacement of the hip bone 12 is for illustration purposes only and the present teachings is applicable to the replacement of the hip bone 14 and to the pelvis 10. From block 302, the method 300, proceeds to block 304.

In block 304, the three-dimensional information, obtained in block 302, is used to fabricate the hip prosthetic 100. It will be appreciated that there are many ways to fabricate the hip 100, such various rapid prototyping systems known to one skilled in the art. Furthermore, the three-dimensional information can be converted to computer-numerical-control (CNC) code can be used in CNC machines. Whichever manufacturing process is used, the hip prosthetic must be made of material that is suitable for implantation into the body and is durable enough for that same purpose. Exemplary materials include, but are not limited to, cobalt chrome, titanium or suitable polymers used for in vivo prosthetics, and known to one skilled in the art. From block 304, the method 300, proceeds to block 306.

In block 306, the prosthetic 100 is prepared along with the area around the healthy hip for receipt of the prosthetic 100. When the hip bone 12, or portions thereof, is resected from the pelvis 10 in preparation for replacement with the hip prosthetic 100, the plurality of bone portions 132 (FIG. 11) connected to the respective connective tissue 128 (FIG. 11) can be left behind to aid re-connection to the hip prosthetic 100. Likewise, portions of the hip prosthetic 100 can also be configured with a plurality of anatomical connection points 310 to mate with the plurality of bone portions 132. This procedure avoids connecting the connective tissue 128 directly to the hip prosthetic 100. It will be appreciated that the anatomical connection points 310 can also be configured as apertures, such that the boney portion 132 can be passed through and attached thereto. After block 306, the method 300 proceeds to block 308.

In block 308, the prosthesis can be implanted and attached to the pelvis 100. The plurality of the bone portions 132 can be attached to the plurality of the anatomical connection points 310. If the hip prosthetic 100 serves as a complete replacement to the hip bone 12, the hip prosthetic 100 can be attached to the sacrum 22, as shown in FIG. 7. If the hip prosthetic 100 serves as a partial replacement to the hip bone 12, the hip prosthetic 100 can be attached to the remaining portions of the hip bone 12, as shown in FIG. 5. Nevertheless, the hip prosthetic 100 is attached to either the sacrum 22 or the remaining portions of the hip bone 12 with the bone screws 110 (FIG. 9) or other suitable fasteners or bonding materials. The pubis member 104 can be attached to the opposed healthy pubis bone 20a. The worm drive 122 can then be tightened to clamp the clamping portion 120 over the opposed healthy pubis bone 20a and secure the hip prosthetic 100.

With reference to FIGS. 23 though 34, the hip prosthetic 100 (FIGS. 4-22) can also be made of a modular multi-component construction generally indicated by reference numeral 400. The modular prosthetic hip 400 includes a pubis clamp component 402, an acetabular component 404, a hip flange component 406 and an extension component 408. In one example, the hip flange component 406 includes a receiving bore 410. Similarly, the pubis clamp component 402 includes a receiving bore 412. The acetabular component 404 includes a first post 414 and a second post 416. The receiving bores 410, 412 and the posts 414, 416 can have complementary tapers that permit the bores 410, 412 to receive the posts 414, 416 and connect thereto. The extension component 408 can also include a post 418 and a receiving bore 420.

It will be appreciated that when the posts 414, 416, 418 are locked to the receiving bores 410, 412, 420 (and suitable combinations), thus forming a taper connection 422, the taper connection 422 therebetween is effectively a fixed connection such that there is substantially no motion between the posts 414, 416, 418 and the receiving bores 410, 412, 420. Moreover, the post/bore connections can be reversed on one or more of the illustrated components. For example, a boss may be formed on the acetabular component 404. The boss may include a bore that receives a complementary taper.

In various examples, components of the modular prosthetic hip 400 can be passed into the surgical area piece by piece and assembled in the surgical area, in some instances, providing a less invasive process.

In one example, the hip flange component 406 defines a connecting flange 424 that can be configured to engage the remaining healthy portions of the hip bone 12 (FIG. 18). Bone screws 110 (FIG. 9) can be similarly secured to the connecting flange 424 and further inserted into the hip bone 12 to secure the modular prosthetic hip 400. Other fasteners, clips, chemical bonding, etc. may be used in lieu of or in combination with one or more of the bone screws 110. The connecting flange 424 can be connected to the hip flange component 406 in various positions, prior to engagement with the extension component 408 or the acetabular component 404, to accommodate the remaining native bone structure. The connecting flange 424 can also be configured in a cup-like and/or a bow-like fashion to further facilitate connection of the native bone structure.

Figure 27:
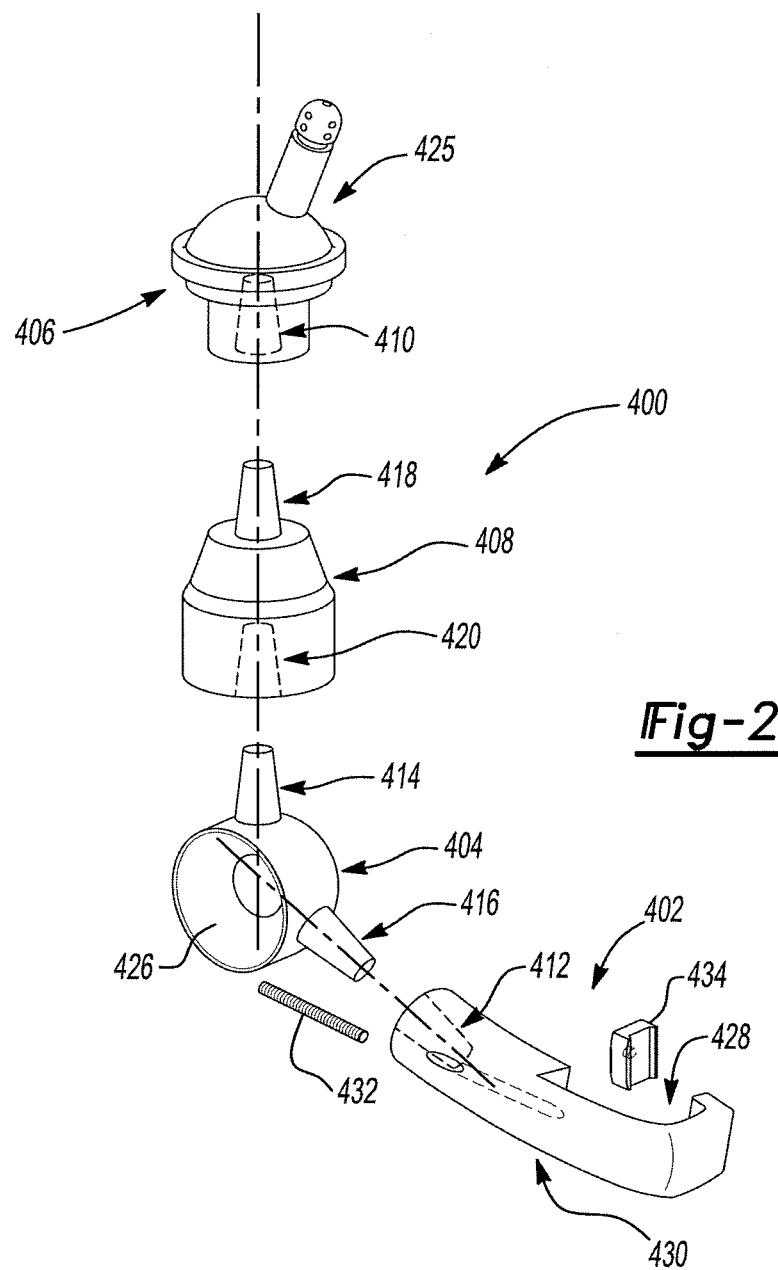
FIG. 27 is similar to FIG. 25 and shows an alternative connection to the hemi-pelvis in accordance with the present teachings.
Figure 28A:
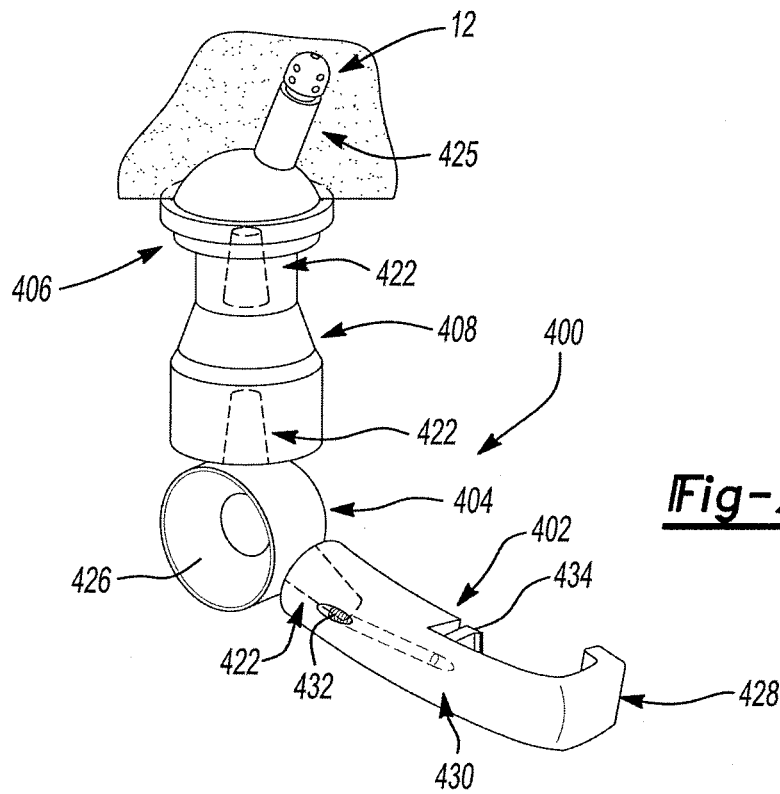
FIGS. 28A, 28B, 28C and 28D are similar to FIG. 27 and show a compliant fixator implanted in the hemi-pelvis with various configuration of the pubic clamp in accordance with the present teachings.
Figure 28B:
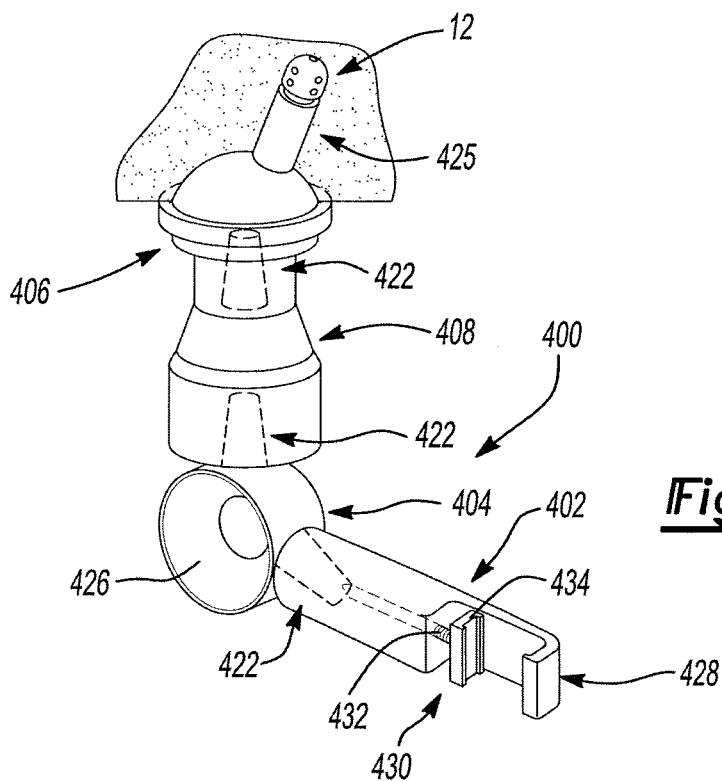
Figure 28C:
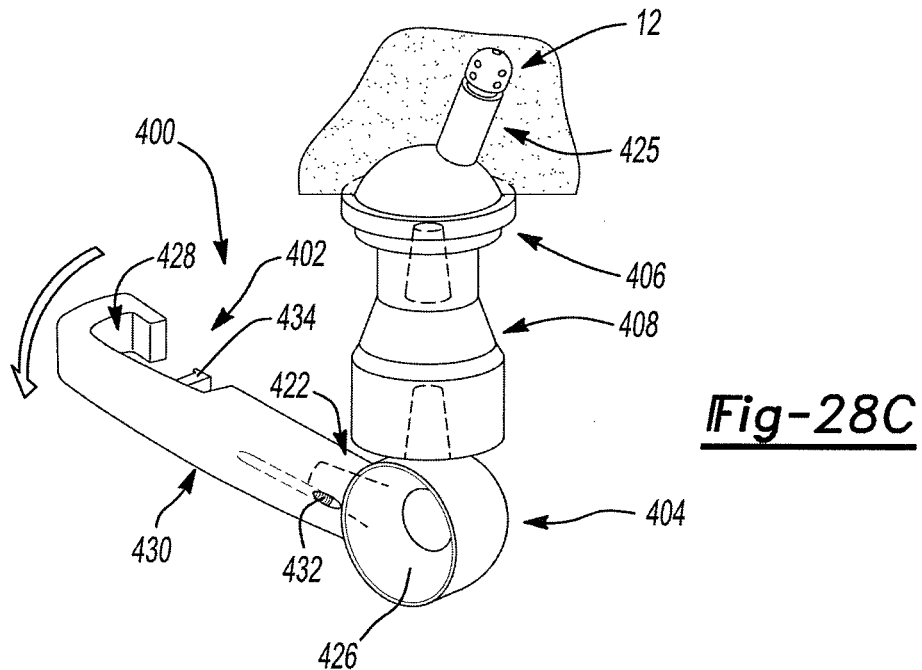
Figure 28D:
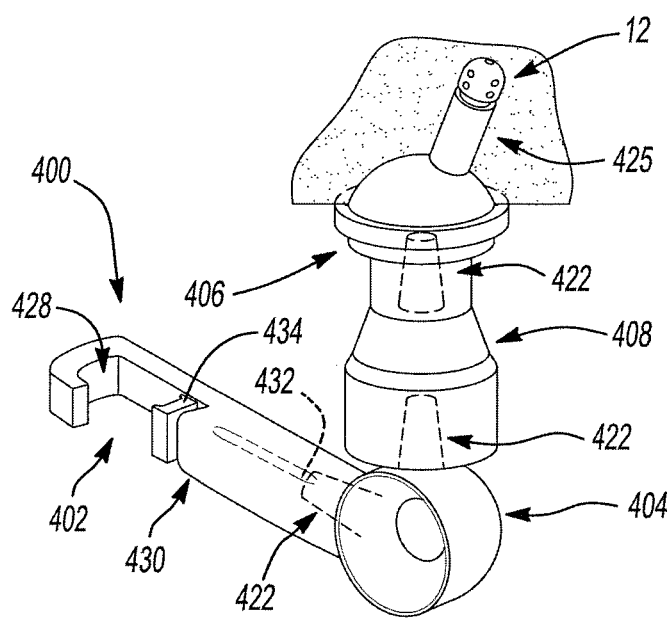
Figure 29:
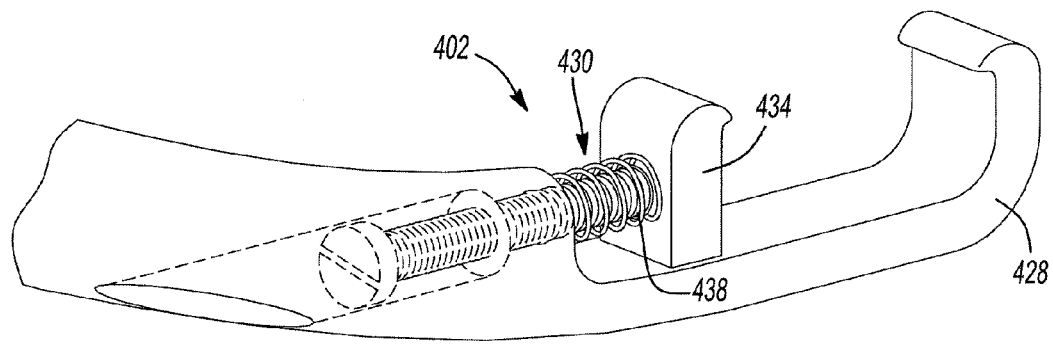
FIG. 29 is similar to FIG. 14 and shows a spring between the catch plate and a portion of the clamping portion to maintain generally consistent pressure against a portion of the native pubis bone in accordance with the present teachings.
Figure 30A:
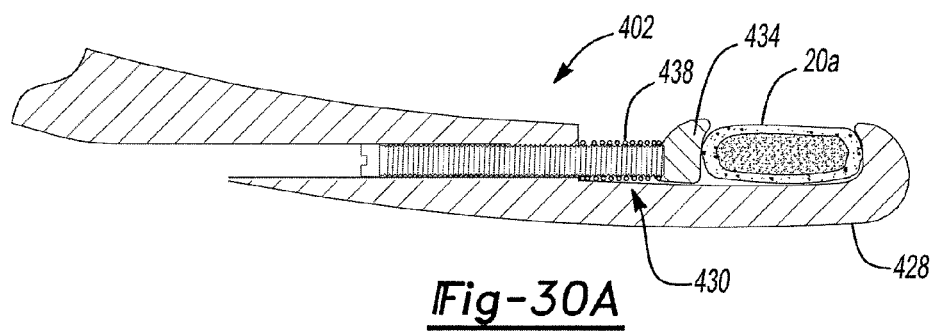
FIGS. 30A and 30B are similar to FIG. 29 and show the catch plate advancing against the native pubis bone when the size of bone may change over time in accordance with the present teachings.
Figure 30B:
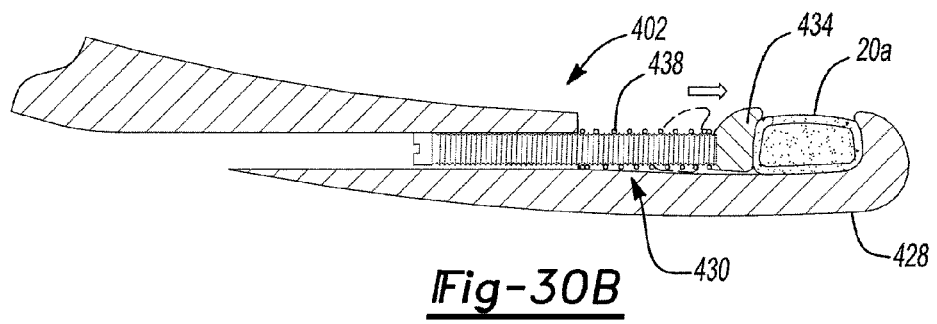

In another example and with reference to FIGS. 27-28D, the hip flange component 406 may include a compliant fixator 425 that connects the acetabular component 404 to portions of the hemi-pelvis. The compliant fixator 425 provides a dynamic load to a portion of the hemi pelvis, such as, for example, a biased compressive load. The compliant fixator 425 can be implanted in a selected area of the hemi-pelvis, for example, the ilium 16 (FIG. 1) at various orientations. The position and orientation of the compliant fixator 425 is not limited to the one illustrated herein but can be selected on the basis of various factors including but not limited to location and availability of healthy bone mass, location requirements for compressive load and bone growth promotion and considerations of interaction with the acetabular component, and functioning of the associated hip joint.

The compliant fixator 425 can be any fixator configured to provide a bone biasing force to a portion of the pelvis 12 (FIG. 1) or otherwise and in particular to the ilium 16 (FIG. 1). Any known compliant fixator can be used including but not limited to the compliant fixators disclosed in co-pending U.S. patent application Ser. No. 10/797,692 or related U.S. Pat. Nos. 6,712,855, 6,508,841, 6,197,065, all of which are assigned to either Biomet, Inc. or Biomet Manufacturing Corp. of Warsaw, Ind. and have already been incorporated by reference.

The acetabular component 404 can include an acetabular cup 426 that accepts a prosthetic femoral head 28a of the femoral component 30c (FIG. 6). The acetabular component 404 can also be configured to receive the acetabular cup 426, i.e., a liner or a multi-piece construction. In one example, the acetabular cup 426 can be positioned and seated in the acetabular component 404 and secured with suitable bone cement or other suitable chemical and/or mechanical fasteners. In other examples, the acetabular cup 426 can be formed integral to (or with) the acetabular component 404. It will be appreciated that integral acetabular cups 426 (i.e., monolithic) may require a plurality of acetabular cups of varying sizes and configurations. When using a multi-piece construction (e.g., a liner connected to the acetabular component), a single acetabular component can be provided along with a plurality of acetabular cups (in one or more pieces) having varying sizes and configuration.

One or more liners 102a (FIG. 6) or bushings can be included with the acetabular component 404 to further facilitate conjunction of the acetabular component 404 to the prosthetic femoral head 28a (FIG. 6). In some examples, the prosthetic femoral head 28a can be attached to the acetabular component 404 using, for example, ring locks or taper junctions. As such, the acetabular component 204 can be configured to directly accept the natural femoral head 28 (FIG. 1). Or, additional liners 102a and/or bushings can be used to facilitate the junction between the acetabular component 404 and the natural femoral head 28.

The clamping portion 428 of the pubis clamp component 402 can be similar to the clamping portion 120 and 220, as shown in FIGS. 14 and 21 respectively. The pubis clamp component 402 can include a worm drive 430. The worm drive 430 can include a threaded rod 432 threaded through the pubis clamp component 402. The threaded rod 432 connects to a catch plate 434. Rotating the worm drive 430 tightens the catch plate 434 against the pubis bone 20a and draws the pubis clamp component 402 closer to the catch plate 434, thus securing the pubis bone 20a in the pubis clamp component 402.

Figure 31:
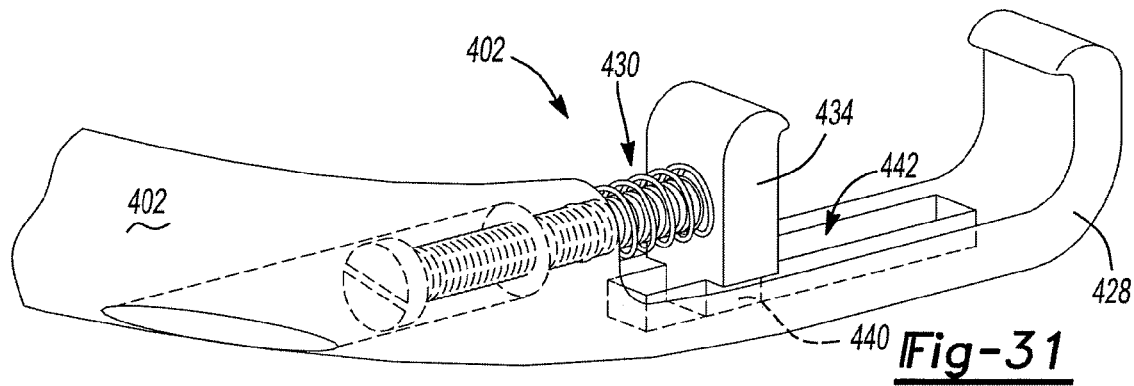
FIG. 31 is similar to FIG. 29 and shows a groove formed on a portion of the pubis clamp in which a portion of the catch plate travels in accordance with the present teachings.
Figure 32:
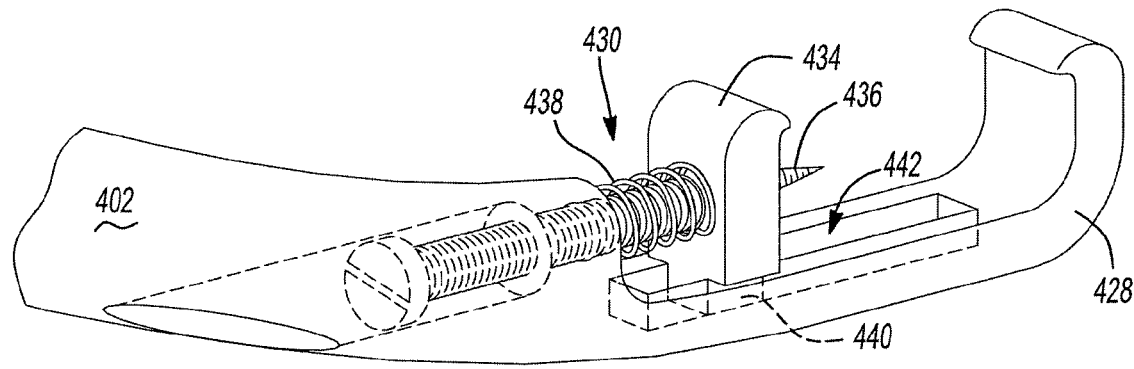
FIG. 32 is similar to FIG. 31 and shows an additional fixation device that can extend from the catch plate and/or the worm drive and attach to the native pubis bone in accordance with the present teachings.
Figure 33:
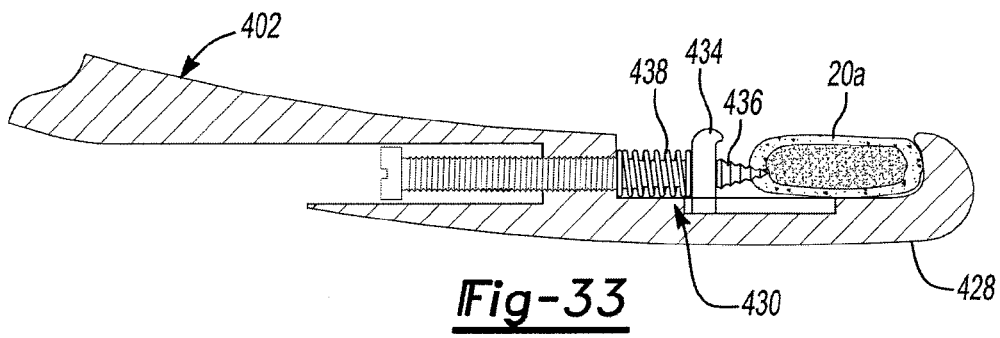
FIG. 33 is similar to FIG. 32 and shows the fixation device attached to the native pubis bone.

In other examples and with reference to FIGS. 31 through 33, the pubis clamp component 402 may include additional fixation devices to attach to or clip onto the native bone 20A. The worm drive 430 and/or the catch plate 434 may include one or more additional mechanical fixation devices to attach to the bone. By rotating the worm drive the additional mechanical fasteners 436, e.g., bone screws, may be inserted into the native bone structure. The additional mechanical fasteners 436 may be in line with the threaded rod 432 or integral with the threaded rod 432. The fasteners 436 may also be separate from the threaded rod 432 and extend from the catch plate 434 and/or the clamping portion 428 to secure the native bone structure.

Figure 32A:
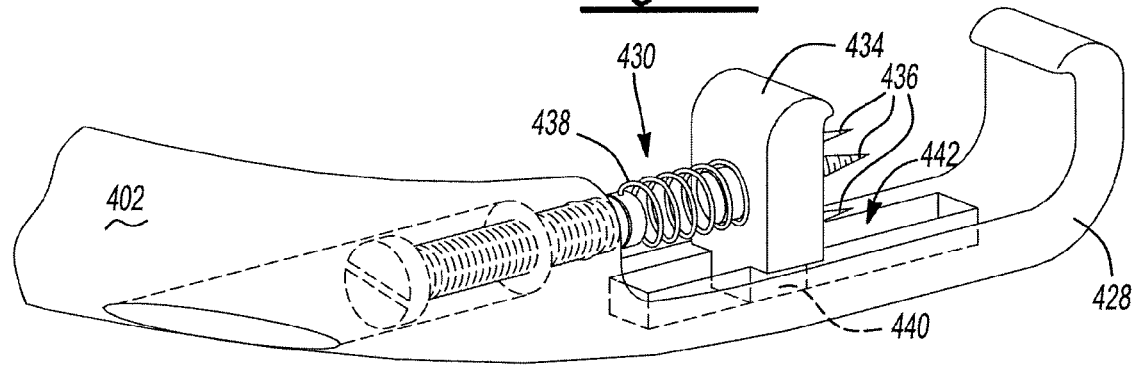
FIG. 32A is similar to FIG. 32 and shows multiple additional fixation devices that can extend from the catch plate and a spring keeper that connects the spring and the catch plate.

A spring 438 may be disposed between a portion of the clamping portion 428 and the catch plate 434 to provide a consistent biasing force against the catch plate 434 and thus against the native bone structure. In FIG. 32A, the spring 438 may be disposed between the threaded rod 432 and the catch plate 434 to provide a biasing force and/or may allow the catch plate 434 to move relative to the threaded rod 432. The additional fixation device and/or the consistent biasing load against the native bone structure may provide for a more secure fit and promote bone growth in and around the catch plate and/or additional fixation device.

In one example, the catch plate 434 may have an additional flange 440 that is received in a channel 442 formed in the pubis clamp component. In this regard, the catch plate 434 travels within the groove 442 via the flange 440 to thus restrict travel of the catch plate 434 within the groove 442. It will be appreciated that the catch plate 434 may or may not be used with the spring 438 as it is secured within the groove and travels therein.

Figure 25:
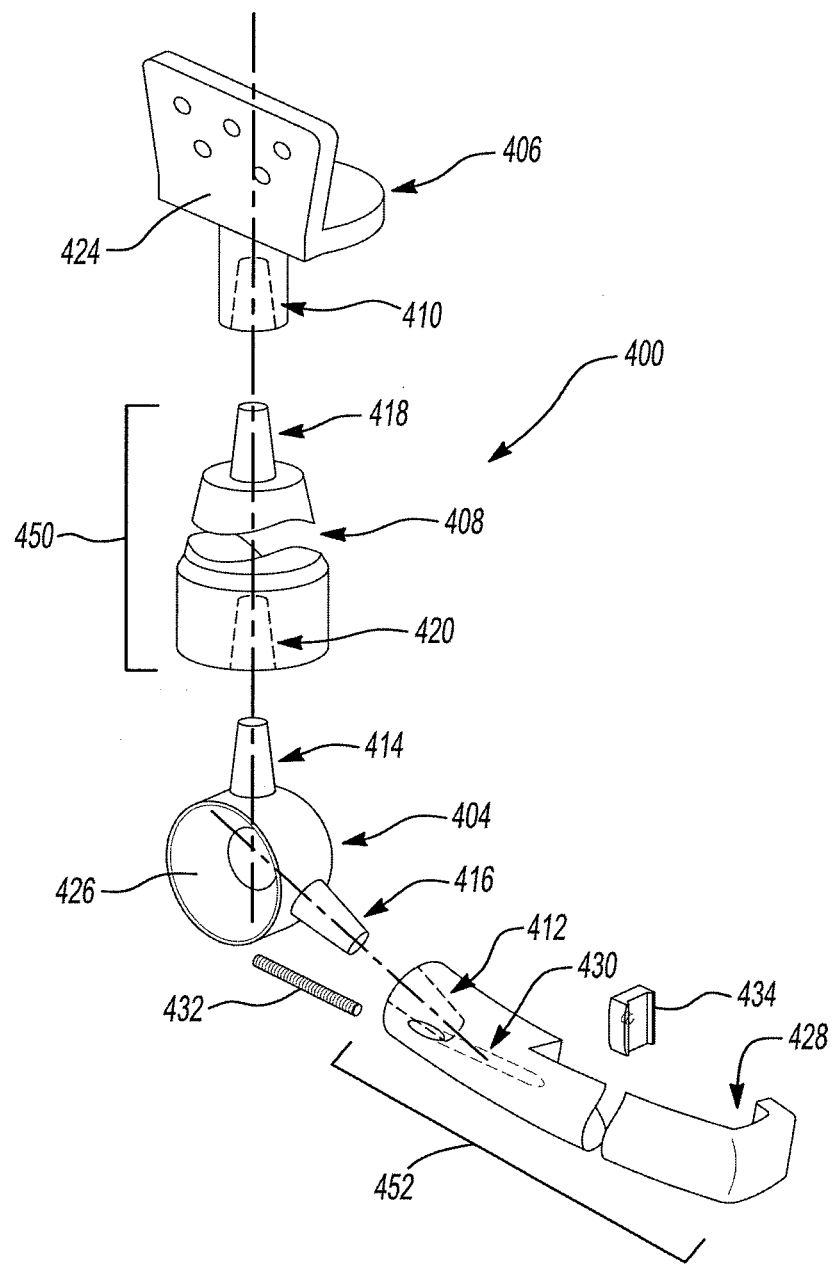
FIG. 25 is similar to FIG. 23 and shows variable sizes and configurations of the components of the partial hip prosthetic.
Figure 26A:
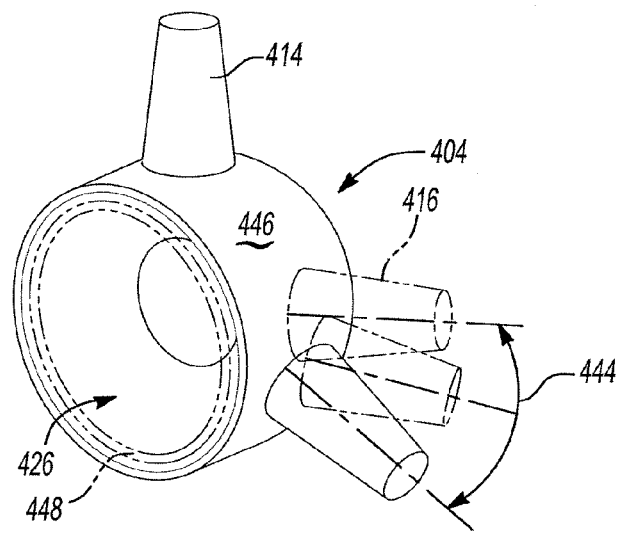
FIG. 26A is a perspective view of the acetabular component of FIG. 23 illustrating various configurations in accordance with the present teachings.
Figure 26B:
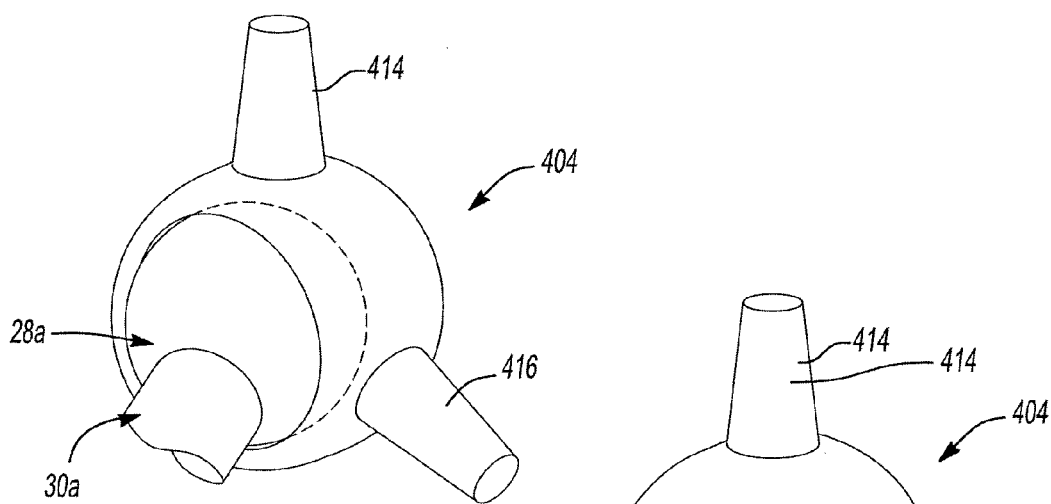
FIGS. 26B and 26C are perspective views of the acetabular component of FIG. 23 illustrating different sizes and configurations of the acetabular component and an exemplary femoral component connected thereto in accordance with the present teachings.
Figure 26C:
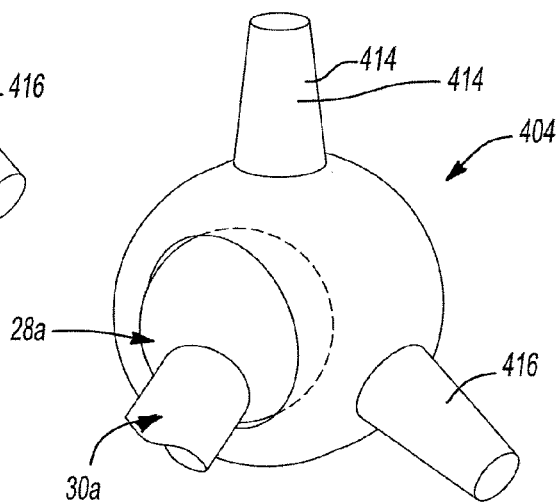

With reference to FIGS. 25 and 26, the various components of the modular prosthetic hip 400 can be sized based on the size of the remaining native bone structure and/or other restrictions that can exist in the operating area. For example, the acetabular component 404 can be configured in different sizes, all of which can be available to the medical professional in a kit or otherwise during or before surgery. The posts 414, 416 can be positioned relative to one another at various circumferential positions (and angles) 444 relative to a surface 446 of the acetabular component 404. The acetabular cup 426 can be configured with various inner diameters 448 and various degrees of concavity and/or circularity. It will be appreciated that the configuration of the acetabular component 404 and the other components of the modular prosthetic hip 400 can be based on the native bone structure that remains and to which the modular prosthetic hip 400 attach.

With reference to FIGS. 28A, 28B, 28C and 28D, the pubis clamp component 402 may be oriented in a direction such that the pubis clamp component 402 can be connected to a native or healthy bone structure on either the anterior or the posterior side of the pelvis. In addition, the pubis clamp component 402 may be rotated such that the clamping portion 428 of the pubis clamp component 402 may latch over or around the native bone structure such that it may come in from the posterior side (FIGS. 28B and 28D) of the structure and loop around to the anterior side of the structure or vice versa (FIGS. 28A and 28C).

With reference to FIG. 25, a length 450 of the extension components 408 and a length 452 of the pubis clamp component 402 can vary. Moreover, one or more extension components 408 can be used between the pubis clamp component 402 and the acetabular component 404 and/or the acetabular component 404 and the hip flange component 406. In one example, the acetabular component 404 can configured with one or more receiving bores and the hip flange component 406 and/or the pubis clamp component 402 can be configured with complementary posts thus forming a similar taper connection or other suitable connection.

With reference to FIGS. 34 and 35, the taper connections may be a substituted for other suitable locking connections that permit the various components of the modular prosthetic 400 to be securely but releasably connected. In one example, the above discussed post and bores may not form complementary tapers but can be secured to one another with a set screw connection. A set screw 454 can be inserted into a set screw aperture 456 formed generally orthogonal (or other suitable orientation) to a receiving bore 458 such that the set screw 454 can be advanced to contact the post 414, 416, 418 received by the receiving bore 458. The post 414, 416, 418 when secured by the set screw 454 can be restricted from moving in a longitudinal and/or rotating direction. It will further be appreciated that any of the above disclosed connections including the taper connections and the set screws along with other suitable connections may be used exclusively or in combination with any or all of the various components of the modular prosthesis. In other examples, the various components may mechanically fasten to one another using any of the above disclosed components, systems, etc., mechanical threads, chemical bonding, welding and suitable combinations thereof to connect the modular components together of the modular prosthesis.

While specific examples have been described in the specification and illustrated in the drawings, it will be understood by those skilled in the art that various changes may be made and equivalents may be substituted for elements thereof without departing from the scope of the present teachings, as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof. Therefore, it may be intended that the present teachings not be limited to the particular examples illustrated by the drawings and described in the specification, as the best mode presently contemplated for carrying out this invention, but that the scope of the present disclosure will include any embodiments falling within the foregoing description and the appended claims.

What is claimed is:

1. A prosthetic device for replacement of a first pelvic portion of a pelvis of a patient opposite to a second pelvic portion relative to a median plane comprising:
    an acetabular component having a first connecting portion and a second connecting portion at an angle relative to the first connecting portion, the angle selected for a corresponding anatomy of the patient;
    a flange component coupled to the first connecting portion and configured to attach to a healthy pelvic portion on a same side of the median plane from the first pelvic portion; and
    a pubis component connected to the second connecting portion of the acetabular component, the pubis component having a first clamping portion and an opposed second clamping portion, wherein the opposed second clamping portion is configured to clamp a portion of a healthy pubis bone to the first clamping portion.

2. The prosthetic device of claim 1, wherein the acetabular component is configured to connect with an acetabular implant.

3. The prosthetic device of claim 1, wherein the acetabular component is configured to connect with a prosthetic femoral head.

4. The prosthetic device of claim 1, wherein the acetabular component is configured to connect with a natural femoral head.

5. The prosthetic device of claim 1, further comprising an acetabular cup configured to connect to the acetabular component.

6. The prosthetic device of claim 1, wherein the acetabular component is fabricated from three-dimensional information obtained from imaging of the second pelvic portion.

7. The prosthetic device of claim 1, wherein the first clamping portion includes an anchoring portion.

8. The prosthetic device of claim 1, wherein the first clamping portion includes a hook.

9. The prosthetic device of claim 1, wherein the first clamping portion is movable relative to the pubis component.

10. The prosthetic device of claim 9, wherein the first clamping portion is spring-biased by a spring.

11. The prosthetic device of claim 10, further comprising a worm drive adjusting biasing of the spring.

12. The prosthetic device of claim 1, further comprising a taper connection between the acetabular component and the pubis component.

13. The prosthetic device of claim 1, wherein the first connecting portion includes a bore for receiving a post from the flange component.

14. The prosthetic device of claim 1, wherein the second connecting portion includes a bore for receiving a post from the pubis component.

15. The prosthetic device of claim 1, wherein the median plane is a vertical longitudinal plane that divides the pelvis into substantially symmetrical halves.

16. A prosthetic device for replacement of a first pelvic portion of a pelvis of a patient opposite to a second pelvic portion relative to a median plane comprising:
    an acetabular component having a first connecting portion and a second connecting portion at an angle relative to the first connecting portion, wherein the acetabular component is fabricated from three-dimensional information obtained from imaging of the second pelvic portion and the angle is selected for a corresponding anatomy of the patient;

a flange component coupled to the first connecting portion and configured to attach to a healthy pelvic portion on a same side of the median plane from the first pelvic portion; and a pubis component connected to the second connecting portion of the acetabular component and having a first clamping portion and an opposed movable portion, wherein the movable portion is configured to clamp a portion of a healthy pubis bone to the first clamping portion and wherein the portion of the healthy pubis bone is clamped to the first clamping portion on an opposite side of the median plane from the first pelvic portion.

17. The prosthetic device of claim 16, wherein the pubis component is fabricated from three-dimensional information obtained from imaging of the second pelvic portion.

18. The prosthetic device of claim 16, wherein the first clamping portion is spring-biased by a spring.

19. A method of replacing a first pelvic portion of a pelvis of a patient opposite to a second pelvic portion relative to a median plane with a prosthetic device, the method comprising:

providing a prosthetic device constructed by imaging of the first and second pelvic portions;

resecting a part of the first pelvic portion such that connective tissues are still attached to a remainder of the first pelvic portion;

forming anatomical connection points on the prosthetic device to substantially match the remainder of the first pelvic portion;

connecting the prosthetic device to the remainder of the first pelvic portion at the connecting points; and providing a first clamping portion and an opposed second clamping portion, wherein the opposed second clamping portion is configured to clamp a portion of a healthy pubis bone to the first clamping portion.

20. The method of claim 19, further comprising coupling an acetabular cup to an acetabular component of the prosthetic device.

21. The method of claim 19, further comprising attaching a flange of the prosthetic device to the first pelvic portion.

* * * * *